United States Patent
Tammana et al.

(10) Patent No.: US 11,097,262 B2
(45) Date of Patent: *Aug. 24, 2021

(54) COMPOSITE HIERARCHICAL ZEOLITE CATALYST FOR HEAVY REFORMATE CONVERSION TO XYLENES

(71) Applicant: Saudi Arabian Oil Company, Dhahran (SA)

(72) Inventors: Veera Venkata Ramakrishna Tammana, Ras Tanura (SA); Raed Hasan Abudawoud, Al-Khobar (SA); Ahmad A. Jazzar, Riyadh (SA); Ahmad Al Mahdi, Dhahran (SA); Thamer A. Mohammad, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 328 days.

This patent is subject to a terminal disclaimer.

(21) Appl. No.: 15/958,394

(22) Filed: Apr. 20, 2018

(65) Prior Publication Data

US 2018/0361372 A1   Dec. 20, 2018

Related U.S. Application Data

(60) Provisional application No. 62/520,155, filed on Jun. 15, 2017.

(51) Int. Cl.
*B01J 29/04* (2006.01)
*B01J 37/00* (2006.01)
(Continued)

(52) U.S. Cl.
CPC .......... *B01J 37/0018* (2013.01); *B01J 29/22* (2013.01); *B01J 29/24* (2013.01); *B01J 29/26* (2013.01); *B01J 29/44* (2013.01); *B01J 29/46* (2013.01); *B01J 29/48* (2013.01); *B01J 29/80* (2013.01); *B01J 35/026* (2013.01); *B01J 35/1057* (2013.01); *B01J 35/1061* (2013.01); *B01J 37/0213* (2013.01); *B01J 37/08* (2013.01); *B01J 37/18* (2013.01); *C01B 39/026* (2013.01); *C07C 6/126* (2013.01); *C07C 15/04* (2013.01); *C07C 15/06* (2013.01); *C07C 15/08* (2013.01); *C10G 35/065* (2013.01); *B01J 29/7034* (2013.01); *B01J 29/7042* (2013.01); *B01J 2229/14* (2013.01); *B01J 2229/183* (2013.01); *B01J 2229/186* (2013.01); *B01J 2229/20* (2013.01);
(Continued)

(58) Field of Classification Search
CPC ... B01J 29/22; B01J 29/24; B01J 29/26; B01J 29/44; B01J 229/46; B01J 29/48; B01J 29/80; B01J 29/7484; B01J 29/7469; B01J 29/7669; B01J 29/7684; B01J 29/7869; B01J 29/7884; B01J 29/041; B01J 29/042; B01J 29/043; B01J 29/044; B01J 29/045; B01J 2229/18; B01J 2229/183; B01J 2229/186; B01J 2229/14; B01J 2229/22; B01J 2229/40; B01J 2229/34; B01J 2229/38; B01J 35/1038; B01J 35/1042; B01J 35/1047; B01J 35/1057; B01J 35/1061; B01J 35/026; B01J 35/109; B01J 37/18; B01J 37/0213; B01J 37/0018; B01J 37/08; B01J 37/0009; B01J 37/031; B01J 37/0201; C01B 39/026; C10G 35/065; C10G 35/095
USPC ........ 502/60, 63, 64, 66, 67, 69, 71, 74, 76, 502/77, 78, 85; 423/702, 704, 709, 710, 423/716
See application file for complete search history.

(56) References Cited

U.S. PATENT DOCUMENTS 4,861,739 A   8/1989  Pellet et al.
6,558,647 B2  5/2003  Lacombe et al.
(Continued)

FOREIGN PATENT DOCUMENTS

CN   103626655 A     3/2014
WO   2006/070073 A1  7/2006
(Continued)

OTHER PUBLICATIONS

Goto et al., "Mesoporous Material from Zeolite", Journal of Porous Materials, 9, 2002, pp. 43-48.*
(Continued)

*Primary Examiner* — Elizabeth D Wood
(74) *Attorney, Agent, or Firm* — Dinsmore & Shohl LLP

(57) ABSTRACT

A method of producing a hierarchical zeolite composite catalyst. The method including dissolving, in an alkaline solution and in the presence of a surfactant, a catalyst precursor comprising mesoporous zeolite to yield a dissolved zeolite solution, where the mesoporous zeolite comprises large pore mordenite and medium pore ZSM-5. The method also including condensing the dissolved zeolite solution to yield a solid zeolite composite from the dissolved zeolite solution and heating the solid zeolite composite to remove the surfactant. The method further including impregnating the solid zeolite composite with one or more active metals selected from the group consisting of molybdenum, platinum, rhenium, nickel, and combinations thereof to yield impregnated solid zeolite composite and calcining the impregnated solid zeolite composite to produce the hierarchical zeolite composite catalyst. The hierarchical zeolite composite catalyst has a mesostructure comprising at least one disordered mesophase and at least one ordered mesophase.

13 Claims, 10 Drawing Sheets

(51) Int. Cl.
| | |
|---|---|
| *B01J 37/02* | (2006.01) |
| *B01J 37/08* | (2006.01) |
| *B01J 35/02* | (2006.01) |
| *B01J 35/10* | (2006.01) |
| *B01J 29/22* | (2006.01) |
| *B01J 29/44* | (2006.01) |
| *B01J 29/48* | (2006.01) |
| *C10G 35/06* | (2006.01) |
| *B01J 29/26* | (2006.01) |
| *C01B 39/02* | (2006.01) |
| *B01J 29/46* | (2006.01) |
| *C07C 6/12* | (2006.01) |
| *B01J 37/18* | (2006.01) |
| *C07C 15/08* | (2006.01) |
| *C07C 15/06* | (2006.01) |
| *B01J 29/24* | (2006.01) |
| *C07C 15/04* | (2006.01) |
| *B01J 29/80* | (2006.01) |
| *B01J 29/70* | (2006.01) |

(52) U.S. Cl.
CPC ........ *B01J 2229/22* (2013.01); *B01J 2229/34* (2013.01); *B01J 2229/38* (2013.01); *B01J 2229/42* (2013.01)

(56) References Cited

U.S. PATENT DOCUMENTS

| | | | |
|---|---|---|---|
| 6,793,911 B2 * | 9/2004 | Koegler | C01B 39/04 423/716 |
| 7,393,989 B2 | 7/2008 | Negiz et al. | |
| 7,589,041 B2 | 9/2009 | Ying et al. | |
| 7,799,961 B2 | 9/2010 | Clark et al. | |
| 7,803,977 B2 | 9/2010 | Riley et al. | |
| 7,807,132 B2 | 10/2010 | Garcia-Martinez | |
| 7,919,421 B2 | 4/2011 | Kalyanaraman et al. | |
| 7,951,986 B2 | 5/2011 | Clark et al. | |
| 7,976,696 B2 | 7/2011 | Ying et al. | |
| 8,071,828 B2 | 12/2011 | Cao et al. | |
| 8,329,973 B2 | 12/2012 | Inui et al. | |
| 8,435,909 B2 | 5/2013 | Al-Khattaf et al. | |
| 8,653,315 B2 | 2/2014 | Ali | |
| 8,697,593 B2 | 4/2014 | Al-Khattaf et al. | |
| 8,821,714 B2 | 9/2014 | Chaumonnot et al. | |
| 9,221,037 B2 | 12/2015 | Ercan et al. | |
| 9,376,324 B2 | 6/2016 | Senderov et al. | |
| 9,573,121 B2 | 2/2017 | Garcia-Martinez | |
| 9,724,680 B2 | 8/2017 | Lai et al. | |
| 9,963,349 B2 | 5/2018 | Boorse et al. | |
| 2002/0018747 A1 * | 2/2002 | Pinnavaia | C10G 47/16 423/702 |
| 2004/0138051 A1 | 7/2004 | Shan et al. | |
| 2005/0234279 A1 | 10/2005 | Serra et al. | |
| 2005/0239634 A1 * | 10/2005 | Ying | C10G 47/02 502/64 |
| 2007/0227351 A1 * | 10/2007 | Garcia-Martinez | C01B 39/023 95/90 |
| 2007/0244347 A1 * | 10/2007 | Ying | B82Y 30/00 585/17 |
| 2008/0138274 A1 * | 6/2008 | Garcia-Martinez | B01J 29/084 423/711 |
| 2008/0214882 A1 | 9/2008 | Pinnavaia et al. | |
| 2009/0005236 A1 * | 1/2009 | Ying | C10G 1/086 502/77 |
| 2009/0090657 A1 * | 4/2009 | Ying | C10G 1/086 208/300 |
| 2009/0326177 A1 * | 12/2009 | Ying | C10G 11/18 526/194 |
| 2010/0092383 A1 * | 4/2010 | Ying | B01J 29/084 423/718 |
| 2011/0118107 A1 | 5/2011 | Garcia-Martinez et al. | |
| 2011/0171121 A1 * | 7/2011 | Senderov | C01B 39/026 423/704 |
| 2011/0201860 A1 | 8/2011 | Akhtar et al. | |
| 2012/0024776 A1 * | 2/2012 | Garcia-Martinez | B01J 20/18 210/500.25 |
| 2012/0258852 A1 | 10/2012 | Martinez et al. | |
| 2013/0090507 A1 | 4/2013 | Ali | |
| 2013/0165315 A1 | 6/2013 | Al-Khattaf et al. | |
| 2013/0281750 A1 | 10/2013 | Abudawoud | |
| 2013/0292300 A1 * | 11/2013 | Ying | B01J 29/005 208/97 |
| 2013/0299389 A1 * | 11/2013 | Garcia-Martinez | B01J 29/084 208/113 |
| 2014/0128246 A1 | 5/2014 | Garcia-Martinez | |
| 2015/0086786 A1 | 3/2015 | Itabashi et al. | |
| 2015/0182953 A1 * | 7/2015 | Senderov | B01J 29/0308 423/714 |
| 2016/0220987 A1 | 8/2016 | Lai et al. | |
| 2016/0221897 A1 | 8/2016 | Elia et al. | |
| 2017/0157598 A1 | 6/2017 | Chal et al. | |
| 2018/0185827 A1 | 7/2018 | Cheng et al. | |

FOREIGN PATENT DOCUMENTS

| | | |
|---|---|---|
| WO | 2011047528 A1 | 4/2011 |
| WO | 2013123299 A1 | 8/2011 |
| WO | 2013151689 A1 | 10/2013 |
| WO | 2013154086 A1 | 10/2013 |
| WO | 2017060464 A1 | 4/2017 |

OTHER PUBLICATIONS

Groen et al., "On the introduction of intracrystalline mesoporosity in zeolites upon desilication in alkaline medium", Microporous and Mesoporous Materials, 69, 2004, pp. 29-34.*

Ogura et al., "Formation of Uniform Mesopores in ZSM-5 Zeolite through Treatment in Alkaline Solution", Chemistry Letters, 2000, pp. 88-883.*

Jacobsen et al., "Mesoporous Zeolite Single Crystals", J. Am. Chem. Soc., 122, 2000, pp. 7116-7117.*

Zhang et al., "Mesoporous Aluminosilicates with Ordered Hexagonal Structure, Strong Acidity, and Extraordinary Hydrothermal Stability at High Temperatures", J. Am. Chem. Soc. 123, 2001, pp. 5014-5021.*

Soler-Illia et al., "Chemical Strategies To Design Textured Materials: From Microporous and Mesoporous Oxides to Nanonetworks and Hierarchical Structures", Chem. Rev., 102, 2002, pp. 4093-4138.*

Corma et al., "From Microporous to Mesoporous Molecular Sieve Materials and Their Use in Catalysis", Chem Rev., 97, 1997, pp. 2373-2419.*

Karlsson et al., "Composites of micro- and mesoporous materials: simultaneous syntheses of MFI/MCM-41 like phases by a mixed template approach", Microporous and Mesoporous Materials, 27, 1999, pp. 181-192.*

Liu et al., "Aluminosilicate mesostructures with improved acidity and hydrothermal stability", J. Mater. Chem., 12, 2002, pp. 3179-3190.*

Notice of Allowance dated Feb. 4, 2020 pertaining to U.S. Appl. No. 15/624,090, filed Jun. 15, 2017, 9 pgs.

Odedairo et al., "Aromatic transformations over aluminosilicate micro/mesoporous composite materials", Catalysis Science & Technology, vol. 2, No. 6, Jan. 1, 2012, pp. 1275-1286, United Kingdom.

Li, et al., "Synthesis of hierarchical mesoporous zeolites based on MOR zeolite: application in the automobile tailpipe hydrocarbon trap", Journal of Porous Materials, vol. 22, No. 3, Apr. 2, 2015, pp. 807-815, Netherlands.

International Search Report and Written Opinion pertaining to International Application No. PCT/US2018/028798 dated Sep. 19, 2018.

Office Action dated Mar. 5, 2019 pertaining to U.S. Appl. No. 15/624,090, filed Jun. 15, 2017, 16 pgs.

Office Action dated Oct. 16, 2019 pertaining to U.S. Appl. No. 15/624,090, filed Jun. 15, 2017, 27 pgs.

(56) References Cited

OTHER PUBLICATIONS

Huang, L. et al. "Investigation of Synthesizing MCM-41/ZSM-5 Composites" J. Phys. Chem. B. 104, 2817-2823 (2000), (Year: 2000).

International Search Report and Written Opiniion dated Jul. 29, 2020 pertaining to International application No. PCT/US2020/026168 filed Apr. 1, 2020, 14 pgs.

Office Action dated May 12, 2020 pertaining to U.S. Appl. No. 16/720,918, filed Dec. 19, 2019, 34 pgs.

Perez-Ramirez, J. et. al., "Tailored Mesoporosity Development in Zeolite Crystals by Partial Detemplation and Desilication", Adv. Fund. Mater 19, 2009, pp. 164-172.

Office Action dated Oct. 27, 2020 pertaining to U.S. Appl. No. 16/720,918, filed Dec. 19, 2019, 17 pgs.

Lidiane Sabina da Silva et al., "Desilication of ZSM-5 and ZSM-12 Zeolites with Different Crystal Sizes: Effect on Acidity and Mesoporous Initiation", Materials Research, 2019, 22(2), pp. 1-9.

Notice of Allowance and Fee(s) Due dated Dec. 30, 2020 pertaining to U.S. Appl. No. 16/720,918, filed Dec. 19, 2019, 3 pgs.

Xu, H et al., "Synthesis of Beta/MCM-41 composite molecular sieve with high hydrothermal stability in static and stirred condition" Journal of Colloid and Interface Science, Jan. 15, 2009, pp. 346-350, vol. 329, No. 2, Academic Press, Inc., US.

Zhang, H et al., "Preparation and characterization of Beta/MCM-41 composite zeolite with a stepwise-distributed pore structure" Powder Technology, Nov. 21, 2007, pp. 73-78, vol. 183, No. 1, Elsevier Sequoia, CH.

International Search Report and Written Opinion pertaining to International Application No. PCT/US2018/036269 dated Nov. 12, 2018.

* cited by examiner

COMPOSITE HIERARCHICAL ZEOLITE CATALYST FOR HEAVY REFORMATE CONVERSION TO XYLENES

CROSS-REFERENCE TO RELATED APPLICATIONS

This application claims the benefit of U.S. Provisional Application Ser. No. 62/520,155 filed Jun. 15, 2017, incorporated herein by reference.

BACKGROUND

Technical Field

Embodiments of the present specification generally relate to zeolite composite catalysts, and specifically relate to zeolite composite catalysts and methods of using the same to convert heavy reformate to xylenes.

Technical Background

Aromatic hydrocarbon compounds derived from petrochemical sources, benzene (C6H6), toluene (methylbenzene, C7H8), and xylenes (dimethylbenzenes, C8H10 isomers) may be used as starting materials for a wide range of consumer products. The xylenes include three isomers of dimethylbenzene, namely: 1,2-dimethylbenzene (orthoxylene or o-xylene), 1,3-dimethylbenzene (meta-xylene or m-xylene), and 1,4-dimethylbenzene (para-xylene or p-xylene). The three isomers of xylene may be used in the synthesis of a number of useful products. For example, upon oxidation, the p-xylene isomer yields terephthalic acid, which may be used in the manufacture of polyester plastics and synthetic textile fibers (such as Dacron®), films (such as Mylar®), and resins (such as polyethylene terephthalate, used in making plastic bottles). The m-xylene isomer may be used in the manufacture of plasticizers, azo dyes, and wood preservers, for example. The o-xylene isomer may be used as a feedstock for phthalic anhydride production, which in turn may be used to make polyesters, alkyl resins, and PVC plasticizers. Therefore, the demand for xylenes remains strong as markets for polyester fibers and polyethylene terephthalate continue to demonstrate high growth rates.

Typically, heavy reformate contains 90 weight (wt.) % to 95 wt. % $C_9$ and 5 wt. % to 10 wt. % $C_{10}$ aromatic compounds. Among the $C_9$ components, trimethylbenzenes (TMBs) (50 wt. % to 60 wt. %) and methylethylbenzenes (MEBs) (30 wt. % to 40 wt. %) are the major constituents. One of the economically viable options is to convert the heavy aromatics in the heavy reformate into valuable products, such as xylenes. Demand is growing faster for xylene derivatives than for benzene derivatives. Therefore, a higher yield of xylenes at the expense of benzene yield is a favorable objective.

Heavy reformate can be subjected to transalkylation either alone or with toluene ($C_7$) for the production of xylenes ($C_8$) and benzene ($C_6$). Because many different compounds may be present in the heavy reformate, multiple parallel and consecutive reactions may take place. Transalkylation reactions for converting aromatic hydrocarbon compounds to compounds having a different number of carbon atoms may include the disproportionation reaction of toluene which is two molecules of toluene reacting to form one molecule of benzene and one molecule of xylene (by transfer of a methyl group from one molecule of toluene to the other, a transalkylation reaction). Transalkylation reactions, however, are not limited to the disproportionation of toluene. Other methods of increasing xylene yields operate through inducing transalkylation by adding aromatic hydrocarbon compounds having nine or more carbon atoms into the starting materials, resulting in such reactions as the addition of one mole of toluene to one mole of a $C_9$ aromatic hydrocarbon to produce two moles of xylene. These parallel and consecutive reaction methodologies may also be accompanied by multiple chemical equilibria, including isomerization of xylenes, TMBs (trimethylbeneze) and MEBs (methylethylbenzene). The transalkylation and disproportionation reactions are equilibrium constrained, while the dealkylation reactions are kinetically controlled.

Regardless, these conventional means to produce xylenes by fractionation of reformate results in a xylene yield that is insufficient to meet the demand, and conversion of other hydrocarbons is necessary to increase the yield of xylenes. Furthermore, xylene isomer streams from catalytic reforming or other sources do not meet the demand as chemical intermediates. Para-xylene in particular is a major chemical intermediate with rapidly growing demand, but equates to only 20% to 25% of a typical $C_8$ aromatics stream.

SUMMARY

Accordingly, ongoing needs exist for catalysts suitable for converting heavy reformates to produce xylenes. Embodiments of the present disclosure are related to heretical zeolite catalysts, their preparation methods and performance, particularly to the synthesis of such catalysts having an ordered/disordered mesostructure and hydrothermal stability. The zeolite composite catalysts may convert a mixture of heavy aromatic compounds (such as those present in heavy reformate), particularly $C_9$ aromatic hydrocarbons to benzene, toluene, and xylenes, and particularly to commercially valuable xylenes. The conversion reactions include dealkylation, transalkylation, disproportionation and isomerization. The zeolite composite catalysts have a high ethyl-dealkylation activity as well as high methyl-transalkylation activity to improve the yield of xylenes.

According to one embodiment, a method of producing a hierarchical zeolite composite catalyst. The method includes dissolving, in an alkaline solution and in the presence of a surfactant, a catalyst precursor comprising mesoporous zeolite while heating, stirring, or both to yield a dissolved zeolite solution. Further, the mesoporous zeolite comprises large pore mordenite, medium pore ZSM-5, or both large pore mordenite and medium pore ZSM-5. The method also includes condensing the dissolved zeolite solution to yield a solid zeolite composite from the dissolved zeolite solution. Condensing the dissolved zeolite solution includes adjusting a pH of the dissolved zeolite solution and aging the pH adjusted dissolved zeolite solution. The method also includes heating the solid zeolite composite to remove the surfactant. Further, the method includes impregnating the solid zeolite composite with one or more active metals selected from the group consisting of molybdenum, platinum, rhenium, nickel, and combinations thereof to yield impregnated solid zeolite composite. Finally, the method includes calcining the impregnated solid zeolite composite to produce the hierarchical zeolite composite catalyst, where the hierarchical zeolite composite catalyst has a mesostructure comprising at least one disordered mesophase and at least one ordered mesophase.

According to another embodiment, a method of converting $C_{9+}$ alkyl aromatic hydrocarbons to a product stream comprising benzene, toluene, and xylene is provided. The method including reducing with hydrogen gas at 400 to 500° C. a hierarchical zeolite composite catalyst having a mesostructure with at least one disordered mesophase and at least one ordered mesophase. The hierarchical zeolite composite catalyst includes large pore mordenite, medium pore ZSM-5, and one or more impregnated active metals. The method further includes contacting a feed comprising $C_{9+}$ alkylaromatic hydrocarbons with the reduced composite zeolite catalyst and hydrogen in a transalkylation zone of a reactor to produce a transalkylation product. Further, the method includes stripping $C_1$-$C_5$ and lighter hydrocarbons and stripping unreacted feed from the transalkylation product and collecting at least the xylenes product from the transalkylation product.

According to yet another embodiment, a hierarchical zeolite composite catalyst is provided. The hierarchical zeolite composite catalyst includes a solid zeolite composite mixed with an alumina binder, the solid zeolite composite having a large pore mordenite and a medium pore ZSM-5 in a 1:1 to 5:1 weight ratio. Further, the hierarchical zeolite composite catalyst has a mesostructure comprising at least one disordered mesophase and at least one ordered mesophase.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Figure 1:
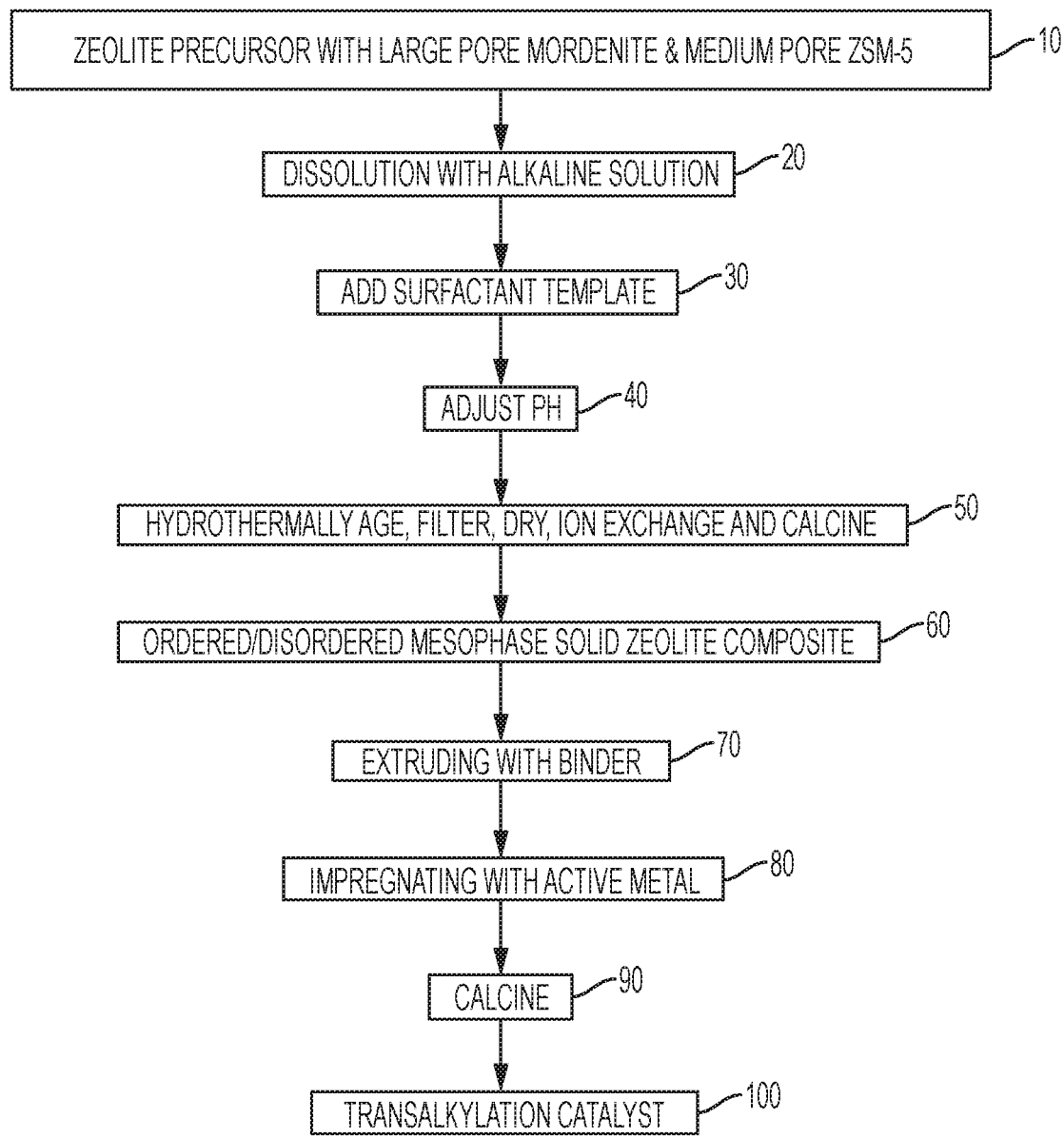
FIG. 1 is a flow chart depicting the synthesis of a zeolite composite catalyst in accordance with one or more embodiments of the present disclosure.

Reference will now be made in detail to embodiments of a hierarchical zeolite composite catalyst comprising a mesostructure comprising at least one disordered mesophase and at least one ordered mesophase. In one embodiment, the ordered mesophase is a hexagonal mesophase, and the disordered mesophase comprises a hexagonal mesophase. Without being bound by theory, hierarchical zeolite composite catalyst with ordered and disordered mesophase formation provides improved transalkylation catalyst activity, which provides improved yield of xylenes. As defined, "ordered mesophase" means a crystalline zeolite uniform arrangement of mesopores, where "mesopores" have an average pore diameter between 2 and 50 nanometers. As defined, "disordered mesophase" means a non-uniform arrangement of pores, where mesopores have an average pore diameter between 2 and 50 nanometers. As defined, "ordered/disordered phase" means the surface has a combination of at least one ordered mesophase and at least one disordered mesophase. Induction of an ordered/disordered phase into the zeolite structure increases the probability of larger molecules in a feed of having access to the active sites inside the hierarchical zeolite composite catalyst. Access to these active sites allows the feed to undergo chemical transformation and decreases the requisite residence time inside the framework of the hierarchical zeolite composite catalyst helping to avoid undesirable side reactions.

Moreover, the hierarchical zeolite composite catalyst may also comprise at least one additional mesoporous zeolite, for example, selected from the group of ZSM-11, ZSM-12, ZSM-22, ZSM-23, MFI topology zeolite, NES topology zeolite, EU-1, MAPO-36, SAPO-5, SAPO-11, SAPO-34, and SAPO-41. The amount of this at least one additional mesoporous zeolite may range from 10 to 90 weight (wt.) % of the hierarchical zeolite composite catalyst in the final dried and calcined form. In further embodiments, the amount of this at least one additional mesoporous zeolite may range from 15 to 80 wt. %, 10 to 30 wt. %, 40 to 90 wt. %, or 10 to 20 wt. % of the hierarchical zeolite composite catalyst in the final dried and calcined form.

Moreover, the hierarchical zeolite composite catalyst may be impregnated with active metals for catalysis, for example, active metals selected from the group consisting of molybdenum, chromium, platinum, nickel, platinum, palladium, rhenium or combinations thereof. In one embodiment, the active metal is molybdenum. The active metal component exists within the final hierarchical zeolite composite catalyst as an elemental metal. The metal component may exist within the final hierarchical zeolite composite catalyst as a compound, such as a metal oxide, a metal sulfide or a metal halide, in chemical combination with one or more of the other ingredients of the hierarchical zeolite composite catalyst, or as the active elemental metal. The metal oxide may be reduced under hydrogen pressure and an elevated temperature, for example 450° C., to from the active elemental metal. The active metal component may be present in the final hierarchical zeolite composite catalyst in any amount that is catalytically effective, generally from 0.01 to 6.0 wt. %, or from 2 to 5 wt. % of the zeolite catalyst.

As described in the synthesis discussion as follows, the hierarchical zeolite composite catalyst may comprise a large pore mordenite and a medium pore ZSM-5 in a 3:1 weight ratio. In further embodiments, the hierarchical zeolite composite catalyst may comprise a large pore mordenite and a medium pore ZSM-5 in a 2:1 weight ratio, a 4:1 weight ratio, a 5:1 weight ratio, or a 1:1 weight ratio. In further embodiments the large pore mordenite or the medium pore ZSM-5 may be provided exclusively. For conciseness of the disclosure, further discussion includes both the large pore mordenite and the medium pore ZSM-5 in combination with the understanding that the large pore mordenite or the medium pore ZSM-5 could be provided individually. In various embodiments, the large pore mordenite may have a Si/Al molar ratio of at least 20, of 20 to 300, of 20 to 100, of 25 to 50, or of 28 to 32. In various embodiments, the medium pore ZSM-5 may have a Si/Al molar ratio of at least 5, of 5 to 500, of 10 to 100, of 20 to 75, of 30 to 50, of 35 to 45, or of 38 to 42.

In one embodiment, the molar ratio of silica to aluminum in the hierarchical zeolite composite catalyst is from 18 to 500. In another embodiment, the molar ratio of silica to aluminum in the hierarchical zeolite composite catalyst is at least 30. Moreover, the molar ratio of silica to aluminum may be from 30 to 100, or from 40 to 80.

From a property standpoint, the hierarchical zeolite composite catalyst may have a surface area defined by a Brunauer-Emmett-Teller (BET) analysis (also known as the Specific Surface Area) of at least 600 meters$^2$ per gram (m$^2$/g), or a BET surface area of at least 700 m$^2$/g. The BET surface area represents the total surface area of a material per unit of mass. Further, the hierarchical zeolite composite catalyst may have an external surface area of at least 300 m$^2$/g, of at least 350 m$^2$/g, of at least 400 m$^2$/g, or 400 to 700 m$^2$/g.

In one or more embodiments, the hierarchical zeolite composite catalyst may have a total pore volume of 0.20 to 3.0 cubic centimeters per gram (cm$^3$/g), or 0.30 to 1.0 cm$^3$/g. Moreover, the hierarchical zeolite composite catalyst may have a total pore volume of at least 0.30 cm$^3$/g, or of at least 0.40 cm$^3$/g, or at least 0.50 cm$^3$/g. In another embodiment, the hierarchical zeolite composite catalyst may have an average pore diameter of at least 30 angstroms (3 nanometers (nm)) or 3 nm to 3.5 nm.

Referring to FIG. 1, the method of producing the hierarchical zeolite composite catalyst may comprise the steps of providing a catalyst precursor 10 comprising a mesoporous zeolite and dissolving in an alkaline solution while heating, stirring, or both to yield a dissolved zeolite solution 20. The mesoporous zeolite may comprise a large pore mordenite and a medium pore ZSM-5. In one embodiment, the catalyst precursor comprises the large pore mordenite and the medium pore ZSM-5 as well as at least one additional mesoporous zeolite selected from the group consisting of ZSM-22, ZSM-12, and combinations thereof. Large pore zeolites are defined as zeolites with 12 membered rings forming the zeolite framework. Medium pore zeolites are defined as zeolites with 10 membered rings forming the zeolite framework. The combination of medium pore zeolite and large pore zeolite provide distinct reaction steps. Specifically, medium pore zeolite, such as ZSM-5, facilitates enhanced dealkylation of ethyltoluenes to produce toluene and large pore zeolites, such as mordenite, facilitates processing of toluene or trimethyl-benezenes into xylenes.

The dissolving step, also called desilication, may be conducted in the presence of a surfactant 30, where the surfactant is often called a templating agent for the zeolite catalyst. While the FIG. 1 embodiment shows templating surfactant, it is contemplated in other embodiments that surfactant is absent. For example and not by way of limitation, the surfactant is a cationic surfactant. The cationic surfactant may include a quaternary ammonium compound. For example and not by way of limitation, the quaternary ammonium cationic surfactant may be cetyltrimethyl ammonium bromide (CTAB). Various amounts of surfactant are contemplated for inclusion in the catalyst precursor. For example, the catalyst precursor may include 1 wt. % to 10 wt. % surfactant, for example CTAB, or 2 wt. % to 8 wt. % surfactant, or 3 wt. % to 6 wt. % surfactant, or 4 wt. % to 5 wt. % surfactant.

During conventional desilication, the mesoporosity in the zeolite is generated by desilication using standard conditions. For example, desilication may be performed using 0.4 Molarity (M) NaOH with 30 minutes (min) of stirring at 100° C. By this process, one third of catalyst is lost due to desilication; however, the present method utilizes that desilicated source to generate mesoporosity using the surfactant template. During a desilication process, loss in the catalyst yield generally occurs due to zeolite dissolution such that approximately 15% of the expected catalyst yield is lost. However, the present methods include recrystallization of the dissolved silica species such that the wasted silica through desilication is effectively utilized and the final yield of hierarchical zeolite composite catalyst is maintained at or near 98%.

Further as shown in FIG. 1, the dissolution may occur slowly in the presence of a surfactant template by gradual heating for 24 hours (h.). The filtrate is collected and mesopores are generated using a template mediated technique. In a template mediated technique, a partially dissolved zeolite is thermally recrystallized around a selected template which dictates the pore size of the regrown structure. In this way, the unutilized desilicated source is utilized to produce the mesophases. Various heating processes or elements are contemplated. For example, the heating may be hydrothermal heating. In one or more embodiments, the hydrothermal heating may occur at a temperature of 50 to 150° C., or a temperature of 90 to 110° C. Furthermore, the duration of hydrothermal heating may range from 30 minutes to 48 hours.

Various alkaline solutions are contemplated for the desilication. In one embodiment, the alkaline solution may comprise NaOH. In specific embodiments, the alkaline solution may comprise 0.01 to 0.5M NaOH, 0.1 to 0.6M NaOH, 0.2 to 0.5M NaOH, 0.35 to 0.45M NaOH, or 0.4M NaOH. Without being bound by theory, it is surprisingly discovered that controlling the molarity of the NaOH is a parameter that impacts the ordered/disordered phase mesostructure of the hierarchical zeolite composite catalyst. It is believed the NaOH is responsible for breaking the chemical structure of the zeolites, thus a larger concentration of the NaOH leads to increased dissolution of the zeolite structure which is recrystallized in the presence of CTAB to form the mesostrucures of the hierarchical zeolite composite catalyst.

Referring again to FIG. 1, the method may comprise the step 40 of adjusting the pH of the dissolved zeolite solution. The adjustment of the pH is performed by an acidic solution. Various acids are contemplated. In one embodiment, the acidic solution comprises sulfuric acid. In one specific embodiment, the acid is 2 Normality (N) (equivalents/liter) dilute sulfuric acid. In specific embodiments, the pH is adjusted to 8 to 10, 8.5 to 9.5, or substantially 9.0.

Next, various additional steps 50 may be utilized, for example, hydrothermal aging, filtering, washing, drying, ion-exchanging and calcining the pH adjusted dissolved zeolite solution. The hydrothermal aging may involve maintaining the pH adjusted dissolved zeolite solution at a temperature of 75 to 125° C. for a duration of 12 to 48 hours. For example, the pH adjusted dissolved zeolite solution may be aged at 100° C. for a duration of 24 hours. During hydrothermal aging, the soluble aluminosilicate species are hydrothermally condensed to form mesophases. The condensing of the dissolved zeolite solution may be performed under still conditions or agitated conditions. Specifically, under still conditions, the dissolved zeolite solution is not stirred or mixed where conversely under agitated conditions the dissolved zeolite solution is mixed or stirred. The solid products formed from condensing the dissolved zeolite solution may be filtered to form a solid zeolite composite, washed thoroughly using distilled water, and then dried. For example, the solid zeolite composite may be dried overnight at a temperature of 100° C. The ion exchange may occur in the presence of a nitrate solution, for example and not by way of limitation, a solution comprising $NH_4NO_3$. In one or more embodiments, the solid zeolite composite is ion exchanged thrice with 0.05M $NH_4NO_3$ solution at 80° C. for 5 hours. The solid zeolite composite may be heated to remove the entrained surfactant. For example, the solid zeolite composite may be heated to 500 to 600° C. for 5 to 8 hours, 570° C. for 7 hours, or 550° C. for 6 hours to vaporize and remove the surfactant template. By stage 60 the solid composite zeolite with ordered/disordered mesophase is formed.

Referring to FIG. 1, the process may also include the step 70 of extruding the solid zeolite composite in the presence of binder. A refractory binder or matrix is optionally utilized to facilitate fabrication of the catalyst, to provide strength, and to reduce fabrication costs. Suitable binders include inorganic oxides, such as one or more of alumina, magnesia, zirconia, chromia, titania, boric, phosphate, zinc oxide and silica. In one embodiment, the binder is an alumina based binder. One commercial embodiment of the alumina binder is Cataloid AP-3, obtained from Catalysts & Chemicals Industries Co., Ltd (CCIC), Japan. The zeolites may be mixed in dry powdered form with the alumina binder in aqueous form to yield a homogeneous mixture, thus ensuring homogeneous composition of the extrudates formed. In one or more embodiments, the ratio by weight of solid zeolite composite to binder is 4 to 1 (80 wt. % solid zeolite composite and 20 wt. % binder), 3 to 1 (75 wt. % solid zeolite composite and 24 wt. % binder), or 2 to 1 (67 wt. % solid zeolite composite and 33 wt. % binder). The extrusion with binder step 70 may be conducted at a temperature of 100 to 150° C. for a duration of 30 minutes to 2 hours.

Next, the process may comprise the step 80 of impregnating solid zeolite composite with one or more active metals prior to a calcining step. The one or more active metals are selected from the group consisting of molybdenum (Mo), platinum (Pt), rhenium (Re), nickel (Ni), and combinations thereof. In one or more embodiments, the active metals comprise 0.01 to 6.0 wt. % of the impregnated solid zeolite composite. In one embodiment, the active metal may comprise molybdenum at 2 to 6% by weight of the impregnated solid zeolite composite, including 4% by weight molybdenum. In one or more embodiments, the solid zeolite composite is impregnated with 4 wt. % of molybdenum in the form of ammonium molybdate tetrahydrate through wet impregnation. Optionally, the impregnated solid zeolite composite may be dried after wet impregnation. In one embodiment, the drying occurs for at least 2 hours at 100° C.

Referring again to FIG. 1, another calcining step 90 may be utilized to produce the hierarchical zeolite composite catalyst, which is effective as a transalkylation catalyst 100. The calcining step may occur for 4 to 8 hours at a temperature of 400 to 500° C., for 4 hours at a temperature of 400° C., for 5 hours at a temperature of 450° C.

Further as stated supra, the present hierarchical zeolite composite catalyst is a transalkylation catalyst suitable for converting $C_{9+}$ alkyl aromatic hydrocarbons to a product stream comprising benzene, toluene, and xylene, particularly to commercially valuable xylenes. The feed stream to the conversion process generally comprises alkylaromatic hydrocarbons in the carbon number range $C_9$ to $C_{11+}$ that may include, for example, such hydrocarbons as propylbenzenes, ethylmethylbenzenes, tetramethylbenzenes, ethyldimethylbenzenes, diethylbenzenes, methylpropylbenzenes, and mixtures thereof. The heavy aromatics feed stream, characterized mainly by $C_{9+}$ aromatics, permits effective transalkylation of light aromatics such as benzene and toluene with the heavier $C_{9+}$ aromatics to yield additional $C_8$ aromatics, such as xylenes. The heavy aromatics stream preferably comprises at least 90 wt. % $C_9$ aromatics, and may be derived from the same or different known refinery and petrochemical processes, and may be recycled from the separation of the product from transalkylation.

Figure 2:
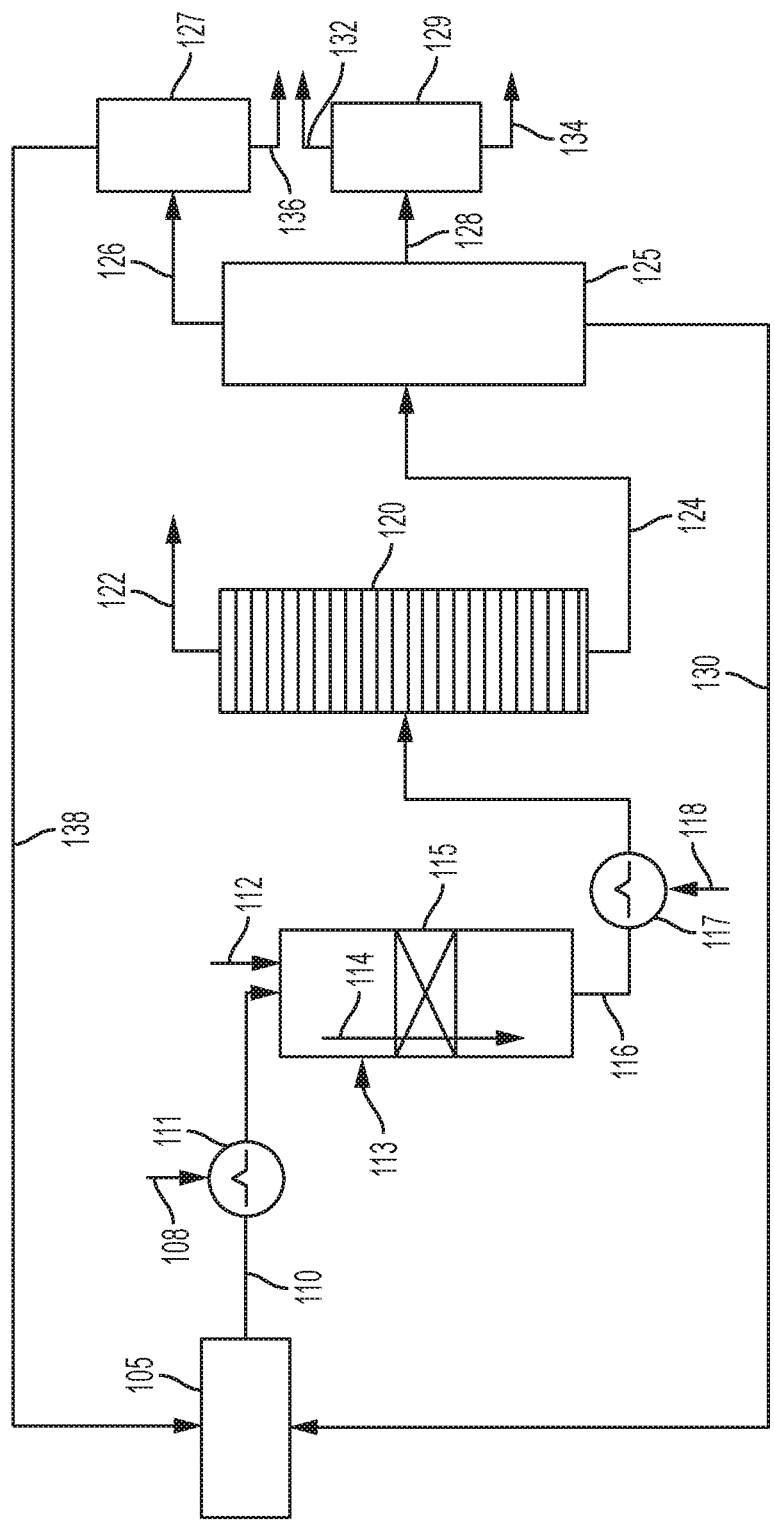
FIG. 2 is a schematic illustration depicting the conversion of heavy reformate into xylenes in accordance with one or more embodiments of the present disclosure.

Referring to the embodiment of FIG. 2, the method of using the hierarchical zeolite composite catalyst as a transalkylation catalyst may optionally include heating a feed stream 110 comprising $C_{9+}$ alkylaromatic hydrocarbons from a feed source 105 with a heater unit 111. As shown, the heater unit 111 may be a heat exchanger which receives a heated stream 108, for example, a heated water stream to heat the feed stream 110 prior to delivery to a reactor 113. The heated stream 108 may also be the effluent of the reaction zone. Other methods of heating the feed are contemplated.

The reactor system may include a reactor 113 with hierarchical zeolite composite catalyst used in transalkylation catalyst zone 115 as shown in FIG. 2, or may include multiple reactors 113 or stages. The reactor 113 is depicted as a downflow 114 reactor but that is one of many possibilities. Similarly, in the embodiment of FIG. 2, the reactor 113 has a fixed cylindrical bed of catalyst; however, other reaction configurations utilizing moving beds of catalyst, radial-flow reactors, or fluidized beds may be employed. Prior to the feed being delivered, the hierarchical zeolite composite catalyst in transalkylation catalyst zone 115 may be reduced, for example, reduced with hydrogen gas 112. In one embodiment, the hierarchical zeolite composite catalyst is reduced by hydrogen gas 112 at a temperature of 350 to 450° C., or 400° C.

Referring again to FIG. 2, the feed stream 110 contacts the reduced hierarchical composite zeolite catalyst and hydrogen 112 in the transalkylation catalyst zone 115 of the reactor 113. Specifically, the feed stream 110 is transalkylated in the vapor phase and in the presence of hydrogen 112. The hydrogen 112 may be delivered with the feed stream 110 in an amount from 0.1 to 10 moles of hydrogen per mole of alkylaromatics. This ratio of hydrogen to alkylaromatics is also referred to as the hydrogen-to-hydrocarbon ratio. The transalkylation results in the production of a transalkylation effluent stream 116 comprising product hydrocarbons, specifically, hydrocarbons having mixed xylene content, as well as unconverted feed, toluene, and benzene. Various conditions are contemplated for the reactor 113. Specifically, the transalkylation catalyst zone 115 may include a temperature between 50° C. and 600° C., 200° C. and 540° C., or 340° C. and 450° C., for example, and moderately elevated pressures of 0.5 megapascal (MPa) to 15.0 MPa, 1.0 MPa to 5.0 MPa, or 1.5 MPa to 3.5 MPa, for example. The liquid hourly space velocity (LHSV) is in the range of 1.0 $hr^{-1}$ to 5.0 $hr^{-1}$ or 1.0 $hr^{-1}$ to 15.0 $hr^{-1}$, for example.

The transalkylation effluent stream 116 may be cooled using a cooler 117. The cooler 117 may be a heat exchanger, condenser, or any other suitable cooling device. As shown, the cooler 117 is a heat exchanger which includes a cooling stream 118. Next, the transalkylation effluent stream 116 may be fed to a stripper column 120, where $C_1$-$C_5$ and lighter hydrocarbons 122 are separated from the transalkylation effluent stream 116.

Referring to FIG. 2, the product 124 of the stripper column 120, which may be discharged from the bottom of the stripper column 120, may include a light recovery stream 126 comprising benzene and toluene, a mixed $C_8$ aromatics product 128, and a heavy recycle stream 130. These all may subsequently be separated in one or more reaction vessels 125, 127, 129. The mixed $C_8$ aromatics product 128 can be sent for recovery of p-xylene 132 and other valuable isomers 134. The light recovery stream 126 may undergo benzene and toluene recovery 136 with the remainder portion recycled as a light recycle stream 138 to the transalkylation zone or the feed source 105. The heavy recycle stream 130 may contain substantially all of the $C_9$ and heavier aromatics and may be partially or totally recycled to the transalkylation reaction zone, or delivered to the feed source 105 for recycle, or removed from the process for disposal or other processing.

EXAMPLES

The described embodiments will be further clarified by the following examples and comparative examples.

For demonstration purposes, the preparation of composite catalysts is provided as follows. The synthesis of Catalyst A, which includes combined treatment of mordenite and ZSM-5 with NaOH followed by still crystallization in CTAB, is described in Example 1. The synthesis of composite Catalyst B which includes combined treatment of mordenite and ZSM-5 with NaOH followed by agitated crystallization in CTAB, is described in Example 2. The synthesis of composite Catalyst C which includes separate treatment of mordenite and ZSM-5 with NaOH followed by still crystallization in CTAB and physical mixing of the separately treated mordenite and ZSM-5 in a 3:1, is presented in Example 3.

The performance of Catalysts A, B, and C were compared with comparative examples representing physical mixtures of untreated constituents of Catalysts A, B, and C (untreated commercial samples of mordenite and ZSM-5) as well as the treated constituents of Catalysts A, B, and C individually (treated mordenite and ZSM-5 individually). The performance of Catalysts A, B and C were compared with one of their constituents (treated mordenite) in Comparative Example 4 (Catalyst D). The performance of Catalysts A, B and C were compared with the other of their constituents (treated ZSM-5) in Comparative Example 5 (Catalyst E). The performance of Catalysts A, B and C were compared with untreated commercial samples of mordenite and ZSM-5 in Comparative Example 6 (Catalyst F). The performance of Catalysts A, B and C were compared with one of their constituents (treated mordenite) and the other constituent untreated (untreated commercial ZSM-5) in Comparative Example 7 (Catalyst G). The performance of Catalysts A, B and C were compared with one of their constituents (treated ZSM-5) and the other constituent untreated (untreated commercial mordenite) in Comparative Example 8 (Catalyst H).

The catalysts described in these examples are exemplary embodiments only, and are not intended to limit the general description of the composite catalyst covering this invention. In each example, the catalyst composition comprises 48.24 wt. % mordenite, 16.08 wt. % ZSM-5, 31.68 wt. % binder, and 4 wt. % active metal except Catalyst D and E where mordenite and ZSM-5 comprise 64.32 wt. %. The binder is an alumina binder (Cataloid, AP-3, obtained from Catalysts & Chemicals Industries Co., Ltd (CCIC), Japan) and the active metal is molybdenum in each example.

TABLE 1

Catalyst compositions

| Catalyst | Constituents | Treatment | Catalyst composition (wt. %) |
|---|---|---|---|
| Catalyst A (Example 1) | Mordenite + ZSM-5 | Combined treatment with 0.4N NaOH Solution followed by still crystallization in the presence of CTAB | Mordenite (48.24%) ZSM-5 (16.08%) Binder (31.68%) Active Metal (4%) |
| Catalyst B (Example 2) | Mordenite + ZSM-5 | Combined treatment with 0.4N NaOH Solution followed by agitated crystallization in the presence of CTAB | Mordenite (48.24%) ZSM-5 (16.08%) Binder (31.68%) Active Metal (4%) |
| Catalyst C (Example 3) | Mordenite + ZSM-5 | Separate treatment with 0.4N NaOH Solution followed by still crystallization in the presence of CTAB | Mordenite (48.24%) ZSM-5 (16.08%) Binder (31.68%) Active Metal (4%) |
| Catalyst D (Comparative Example 4) | Mordenite | Treatment with 0.4N NaOH Solution followed by still crystallization in the presence of CTAB | Mordenite (64.32%) Binder (31.68%) Active Metal (4%) |
| Catalyst E (Comparative Example 5) | ZSM-5 | Treatment with 0.4N NaOH Solution followed by still crystallization in the presence of CTAB | ZSM-5 (64.32%) Binder (31.68%) Active Metal (4%) |

TABLE 1-continued

Catalyst compositions

| Catalyst | Constituents | Treatment | Catalyst composition (wt. %) |
|---|---|---|---|
| Catalyst F (Comparative Example 6) | Mordenite + ZSM-5 | Not treated, Commercial samples physically mixed | Mordenite (48.24%) ZSM-5 (16.08%) Binder (31.68%) Active Metal (4%) |
| Catalyst G (Comparative Example 7) | Mordenite + ZSM-5 | Only mordenite treated with 0.4N NaOH Solution followed by still crystallization in the presence of CTAB and physically mixed with untreated commercial ZSM-5 | Mordenite (48.24%) ZSM-5 (16.08%) Binder (31.68%) Active Metal (4%) |
| Catalyst H (Comparative Example 8) | Mordenite + ZSM-5 | Only ZSM-5 treated with 0.4N NaOH Solution followed by still crystallization in the presence of CTAB and physically mixed with untreated commercial mordenite | Mordenite (48.24%) ZSM-5 (16.08%) Binder (31.68%) Active Metal (4%) |

Example 1: Combined Treatment of Mordenite and ZSM-5 with 0.4 N NaOH Solution Followed by Still Crystallization in the Presence of CTAB Three grams of mordenite (Si/Al molar ratio=30), HSZ-660HOA, available from Tosoh Corporation, Japan, and one gram ZSM-5 (Si/Al molar ratio=40), HSZ-840NHA, available from Tosoh Corporation, Japan, were disintegrated using 0.40M NaOH solution by gradual heating (without stirring) at 100° C. for 24 hours (h). The heating was carried out in the presence of CTAB (4.45 wt. %). The mixture was cooled down and then the pH was adjusted to 9.0 through the addition of dilute sulfuric acid (2N). The mixture was then stirred for 24 hours (h) and then aged at 100° C. for 24 h to form a solid zeolite composite. The solid zeolite composite was filtered, washed thoroughly using distilled water, dried at 80° C. overnight, then calcined at 570° C. for 7 h to remove the surfactant (CTAB). The solid composite material thus obtained was ion-exchanged three times with 0.05 M NH4NO3 solution at 80° C. for 5 h. The resulting zeolite meso-structured mordenite and ZSM-5 was made into extrudates by mixing 67 wt. % solid zeolite composite and 33 wt. % alumina binder (Cataloid AP-3) and then loaded with 4 wt. % of molybdenum in the form of ammonium molybdate tetrahydrate through wet impregnation. Then, the impregnated solid zeolite was calcined at 450° C. for 5 h. The resulting zeolite mordenite/ZSM-5 composite is designated as Example 1 (Catalyst A). Table 2 includes selected properties of Example 1 (Catalyst A).

TABLE 2

Example 1 (Catalyst A) Data

| Catalyst | BET Surface Area (m²/g) | Micropore Surface Area (m²/g) | External Surface Area (m²/g) | Total Pore Volume (cm³/g) | Micropore Volume (cm³/g) | Mesopore Volume (cm³/g) |
|---|---|---|---|---|---|---|
| Example 1 (Catalyst A) | 533 | 288 | 245 | 0.5519 | 0.128 | 0.4239 |

Figure 3:
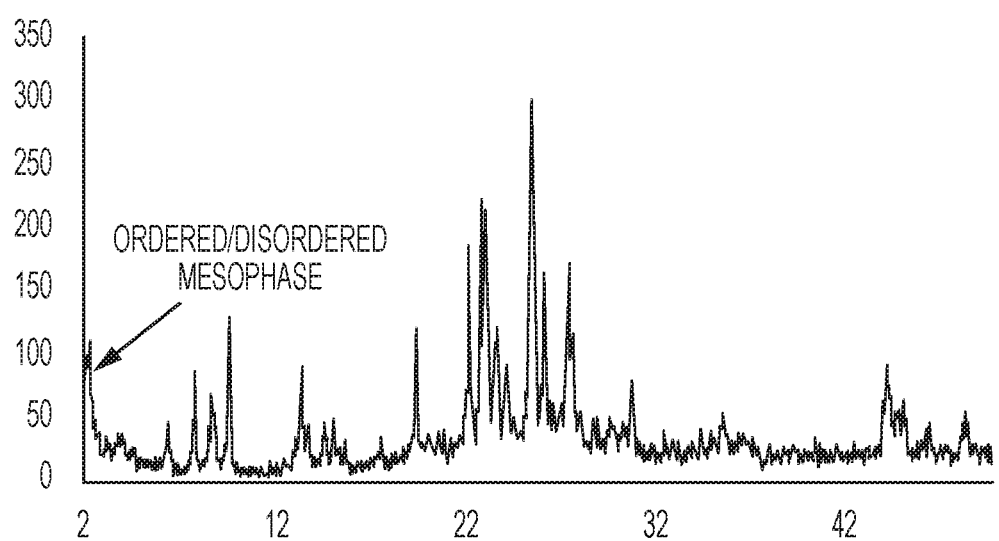
FIG. 3 is an X-Ray Diffraction (XRD) graph of a zeolite composite catalyst having an ordered hexagonal mesophase and a disordered hexagonal mesophase, which was produced through the dissolution of mordenite and ZSM-5 in a 3:1 ratio using 0.4 Molarity (M) NaOH solution in the presence of still CTAB in accordance with one or more embodiments of the present disclosure.

The dissolution of mordenite and ZSM-5 using 0.40M NaOH solution and still crystallization in the presence of CTAB leads to meso-structure formation with ordered and disordered mesophase as shown in FIG. 3. The XRD pattern indicates the formation of meso-structure based on the position of the indicated peak and the shape of the indicated peak indicates the ordered and disordered mesophase.

Example 2: Combined Treatment of Mordenite and ZSM-5 with 0.4 N NaOH Solution Followed by Agitated Crystallization in the Presence of CTAB Three grams of mordenite (Si/Al molar ratio=30), HSZ-660HOA, and one gram ZSM-5 (Si/Al molar ratio=40), HSZ-840NHA, were disintegrated using 0.40M NaOH solution by gradual heating (with stirring) at 100° C. for 24 hours (h). The heating was carried out in the presence of CTAB (4.45 wt. %). The mixture was cooled down and then the pH was adjusted to 9.0 through the addition of dilute sulfuric acid (2N). The mixture was then stirred for 24 hours (h) and then aged at 100° C. for 24 h to form a solid zeolite composite. The solid zeolite composite was filtered, washed thoroughly using distilled water, dried at 80° C. overnight, then calcined at 570° C. for 7 h to remove the surfactant (CTAB). The solid composite material thus obtained was ion-exchanged three times with 0.05 M NH4NO3 solution at 80° C. for 5 h. The resulting zeolite meso-structured mordenite and ZSM-5 was made into extrudates by mixing 67 wt. % solid zeolite composite and 33 wt. % alumina binder (Cataloid AP-3) and then loaded with 4 wt. % of molybdenum in the form of ammonium molybdate tetrahydrate through wet impregnation. Then the impregnated solid zeolite was calcined at 450° C. for 5 h. The resulting zeolite mordenite/ZSM-5 composite is designated as Example 2 (Catalyst B). Table 3 includes selected properties of Example 2 (Catalyst B).

TABLE 3

Example 2 (Catalyst B) Data

| Catalyst | BET Surface Area (m²/g) | Micropore Surface Area (m²/g) | External Surface Area (m²/g) | Total Pore Volume (cm³/g) | Micropore Volume (cm³/g) | Mesopore Volume (cm³/g) |
|---|---|---|---|---|---|---|
| Example 2 (Catalyst B) | 550 | 280 | 260 | 0.5826 | 0.132 | 0.4506 |

Figure 4:
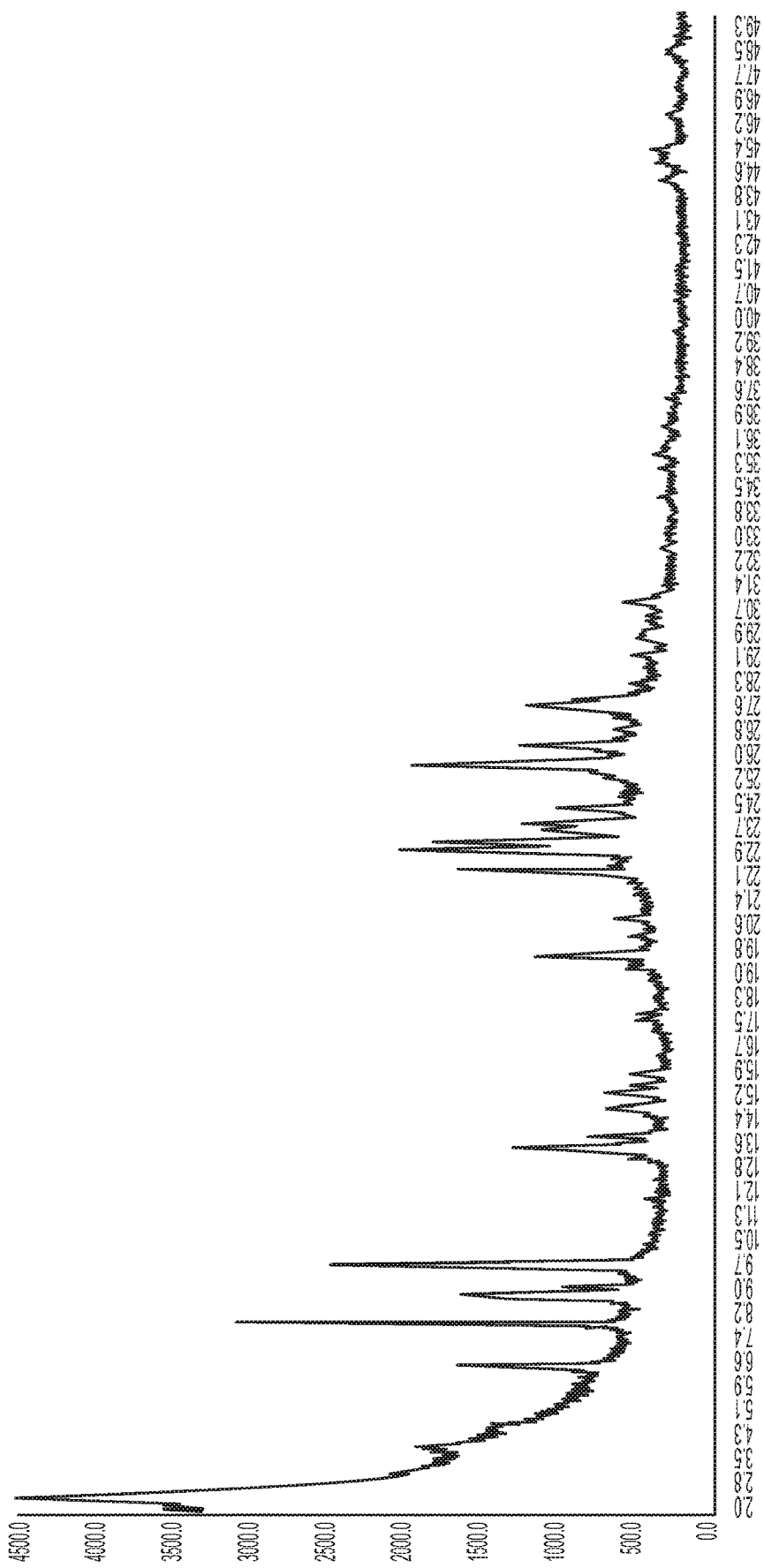
FIG. 4 is an XRD graph of a zeolite composite catalyst having an ordered hexagonal mesophase and a disordered hexagonal mesophase, which was produced through the dissolution of mordenite and ZSM-5 in a 3:1 ratio using 0.4M NaOH solution in the presence of agitated CTAB in accordance with one or more embodiments of the present disclosure.

The dissolution of mordenite and ZSM-5 using 0.40M NaOH solution and agitated crystallization in the presence of CTAB leads to meso-structure formation with ordered and disordered mesophase as shown in FIG. 4. The XRD pattern indicates the formation of meso-structure based on the position of the indicated peak and the shape of the indicated peak indicates the ordered and disordered mesophase.

Example 3: Separate Treatment of Mordenite and ZSM-5 with 0.4 N NaOH Solution Followed by Still Crystallization in the Presence of CTAB In separate glass vessels, three grams of mordenite (Si/Al molar ratio=30), HSZ-660HOA, and one gram ZSM-5 (Si/Al molar ratio=40), HSZ-840NHA, were respectively disintegrated using 0.40M NaOH solution by gradual heating (without stirring) at 100° C. for 24 hours (h). The heating was carried out in the presence of CTAB (4.45 wt. %). Each mixture was cooled down and then the pH was adjusted to 9.0 through the addition of dilute sulfuric acid (2N). Each mixture was then stirred for 24 hours (h) and then aged at 100° C. for 24 h to form a solid zeolite composite of mordenite and ZSM-5 respectively. The solid zeolite composites were individually filtered, washed thoroughly using distilled water, dried at 80° C. overnight, then calcined at 550° C. for 6 h to remove the surfactant (CTAB). Each solid composite material (mordenite and ZSM-5) thus obtained was ion-exchanged three times with 0.05 M NH4NO3 solution at 80° C. for 5 h. The resulting zeolite meso-structured mordenite and ZSM-5 were physically mixed in a 3:1 ratio and made into extrudates by mixing 67 wt. % solid zeolite composite (mordenite+ZSM-5 at 3:1 ratio) and 33 wt. % alumina binder (Cataloid AP-3) and then loaded with 4 wt. % of molybdenum in the form of ammonium molybdate tetrahydrate through wet impregnation. Then, the impregnated solid zeolite was calcined at 450° C. for 5 h. The resulting zeolite mordenite/ZSM-5 composite is designated as Example 3 (Catalyst C).

Table 4 includes selected properties of Example 3 (Catalyst C).

TABLE 4

Example 3 (Catalyst C) Data

| Catalyst | BET Surface Area (m²/g) | Micropore Surface Area (m²/g) | External Surface Area (m²/g) | Total Pore Volume (cm³/g) | Micropore Volume (cm³/g) | Mesopore Volume (cm³/g) |
|---|---|---|---|---|---|---|
| Example 3 (Catalyst C) | 641 | 220 | 421 | 0.8573 | 0.099 | 0.7583 |

Figure 5:
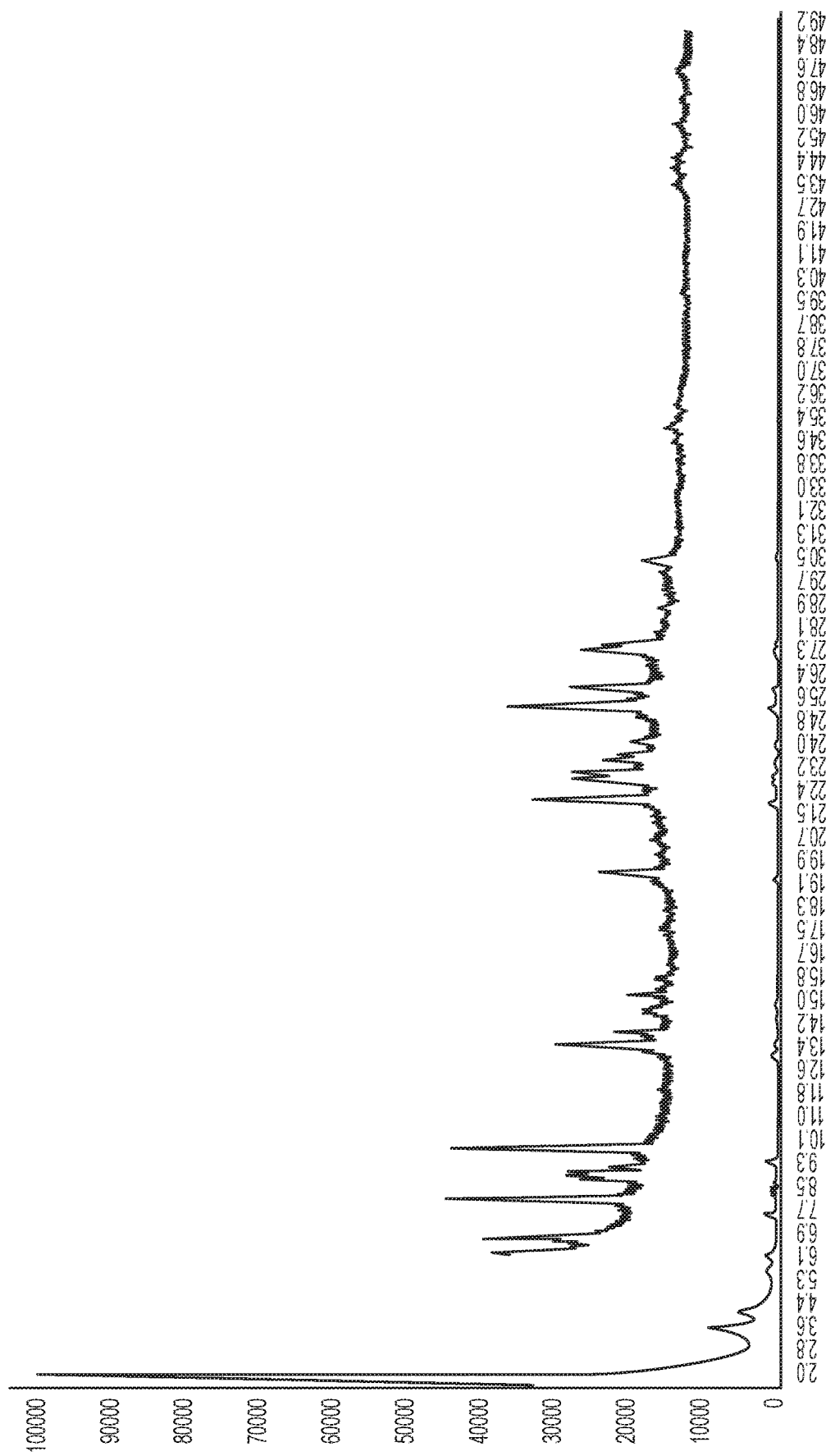
FIG. 5 is an XRD graph of a zeolite composite catalyst having an ordered hexagonal mesophase and a disordered hexagonal mesophase, which was produced through the dissolution of mordenite and ZSM-5 separately using 0.4M NaOH solution in the presence of still CTAB and then physically mixed in a 3:1 ratio in accordance with one or more embodiments of the present disclosure.

The separate dissolution of mordenite and ZSM-5 using 0.40M NaOH solution and still crystallization in the presence of CTAB leads to meso-structure formation with ordered and disordered mesophase as shown in the XRD pattern in FIG. 5. The mordenite and ZSM-5 are provide as a physical mixture in a 3:1 ratio in FIG. 5.

Comparative Example 4: Treatment of Mordenite with 0.4 N NaOH Solution Followed by Still Crystallization in the Presence of CTAB Mordenite (Si/Al molar ratio=30), HSZ-660HOA, was disintegrated using 0.40M NaOH solution by gradual heating (without stirring) at 100° C. for 24 hours (h). The heating was carried out in the presence of CTAB (4.45 wt. %). The mixture was cooled down and then the pH was adjusted to 9.0 through the addition of dilute sulfuric acid (2N). The mixture was then stirred for 24 hours (h) and then aged at 100° C. for 24 h to form a solid zeolite composite. The solid zeolite composite was filtered, washed thoroughly using distilled water, dried at 80° C. overnight, then calcined at 570° C. for 7 h to remove the surfactant (CTAB). The solid composite material thus obtained was ion-exchanged three times with 0.05 M NH4NO3 solution at 80° C. for 5 h. The resulting zeolite meso-structured mordenite was made into extrudates by mixing 67 wt. % mordenite and 33 wt. % alumina binder (Cataloid AP-3) and then loaded with 4 wt. % of molybdenum in the form of ammonium molybdate tetrahydrate through wet impregnation. Then, the impregnated solid zeolite was calcined at 450° C. for 5 h. The resulting zeolite mordenite composite is designated as Comparative Example 4 (Catalyst D). Table 5 includes selected properties of Comparative Example 4 (Catalyst D).

TABLE 5

Comparative Example 4 (Catalyst D) Data

| Catalyst | BET Surface Area (m²/g) | Micropore Surface Area (m²/g) | External Surface Area (m²/g) | Total Pore Volume (cm³/g) | Micropore Volume (cm³/g) | Mesopore Volume (cm³/g) |
|---|---|---|---|---|---|---|
| Comparative Example 4 (Catalyst D) | 622 | 240 | 382 | 0.7724 | 0.139 | 0.6334 |

Figure 6:
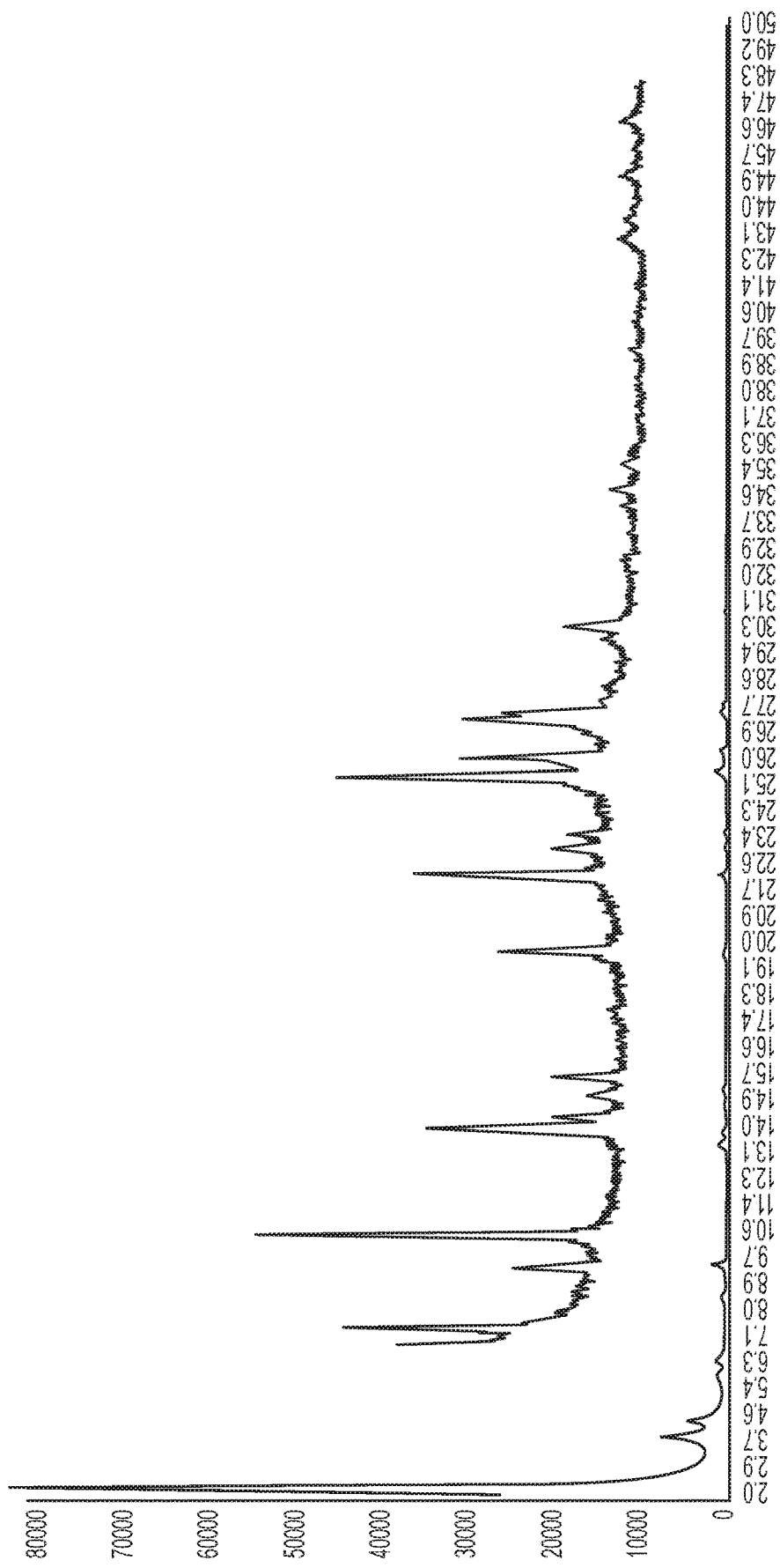
FIG. 6 is an XRD graph of a zeolite catalyst having an ordered hexagonal mesophase and a disordered hexagonal mesophase, which was produced through the dissolution of mordenite using 0.4M NaOH solution in the presence of CTAB.

The dissolution of mordenite using 0.40M NaOH solution and still crystallization in the presence of CTAB leads to meso-structure formation with ordered and disordered mesophase as shown in the XRD pattern in FIG. 6.

Comparative Example 5: Treatment of ZSM-5 with 0.4 N NaOH Solution Followed by Still Crystallization in the Presence of CTAB ZSM-5 (Si/Al molar ratio=40), HSZ-840NHA, was disintegrated using 0.40M NaOH solution by gradual heating (without stirring) at 100° C. for 24 hours (h). The heating was carried out in the presence of CTAB (4.45 wt. %). The mixture was cooled down and then the pH was adjusted to 9.0 through the addition of dilute sulfuric acid (2N). The mixture was then stirred for 24 hours (h) and then aged at 100° C. for 24 h to form a solid zeolite composite. The solid zeolite composite was filtered, washed thoroughly using distilled water, dried at 80° C. overnight, then calcined at 570° C. for 7 h to remove the surfactant (CTAB). The solid composite material thus obtained was ion-exchanged three times with 0.05 M NH4NO3 solution at 80° C. for 5 h. The resulting zeolite meso-structured ZSM-5 was made into extrudates by mixing 67 wt. % ZSM-5 and 33 wt. % alumina binder (Cataloid AP-3) and then loaded with 4 wt. % of molybdenum in the form of ammonium molybdate tetrahydrate through wet impregnation. Then, the impregnated solid zeolite was calcined at 450° C. for 5 h. The resulting zeolite ZSM-5 composite is designated as Comparative Example 5 (Catalyst E). Table 6 includes selected properties of Comparative Example 5 (Catalyst E).

TABLE 6

Comparative Example 5 (Catalyst E) Data

| Catalyst | BET Surface Area (m²/g) | Micropore Surface Area (m²/g) | External Surface Area (m²/g) | Total Pore Volume (cm³/g) | Micropore Volume (cm³/g) | Mesopore Volume (cm³/g) |
|---|---|---|---|---|---|---|
| Comparative Example 5 (Catalyst E) | 655 | 256 | 399 | 1.024 | 0.146 | 0.878 |

Figure 7:
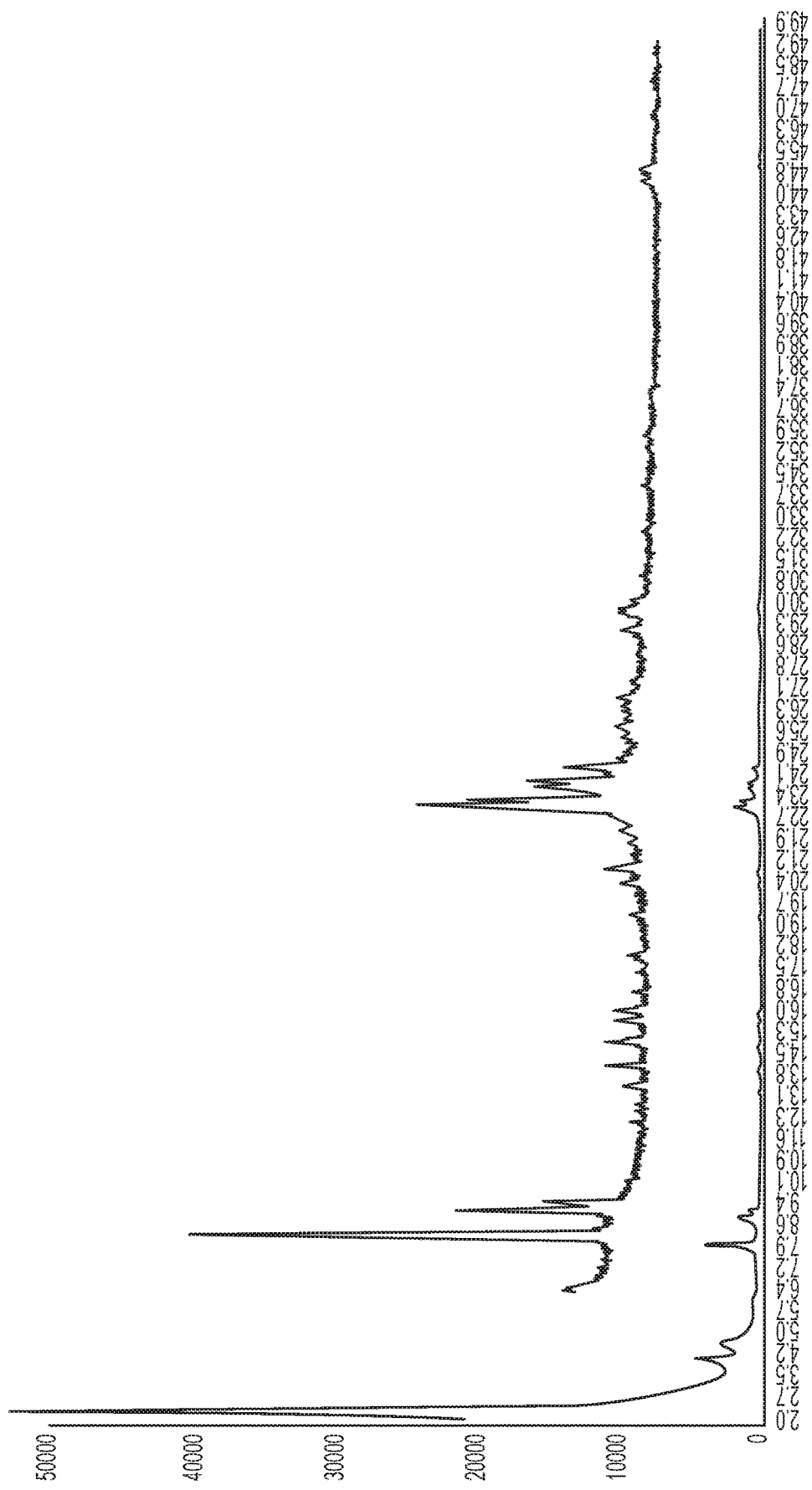
FIG. 7 is an XRD graph of a zeolite catalyst having an ordered hexagonal mesophase and a disordered hexagonal mesophase, which was produced through the dissolution of ZSM-5 using 0.4M NaOH solution in the presence of CTAB.

The dissolution of ZSM-5 using 0.40M NaOH solution and still crystallization in the presence of CTAB leads to meso-structure formation with ordered and disordered mesophase as shown in the XRD pattern in FIG. 7.

Comparative Example 6: Untreated, Commercial Samples of Mordenite and ZSM-5 Physically Mixed Untreated forms of mordenite (HSZ-660 HOA, Tosoh Chemicals) and ZSM-5 (HSZ-840 NHA, Tosoh Chemicals) in their ammoniated forms were physically mixed in a 3:1 weight ratio and made into extrudates by mixing 67 wt. % zeolite mixture (untreated mordenite+untreated ZSM-5 at a 3:1 weight ratio) and 33 wt. % alumina binder (Cataloid AP-3) and then loaded with 4 wt. % of molybdenum in the form of ammonium molybdate tetrahydrate through wet impregnation. Then, the impregnated solid zeolite was calcined at 450° C. for 5 h. The resulting zeolite mordenite/ZSM-5 composite is designated as Comparative Example 6 (Catalyst F). Table 6 includes selected properties of Comparative Example 6 (Catalyst F).

TABLE 7

Comparative Example 6 (Catalyst F) Data

| Catalyst | BET Surface Area ($m^2/g$) | Micropore Surface Area ($m^2/g$) | External Surface Area ($m^2/g$) | Total Pore Volume ($cm^3/g$) | Micropore Volume ($cm^3/g$) | Mesopore Volume ($cm^3/g$) |
|---|---|---|---|---|---|---|
| Comparative Example 6 (Catalyst F) | 405 | 370 | 35 | 0.2455 | 0.179 | 0.0665 |

Figure 8:
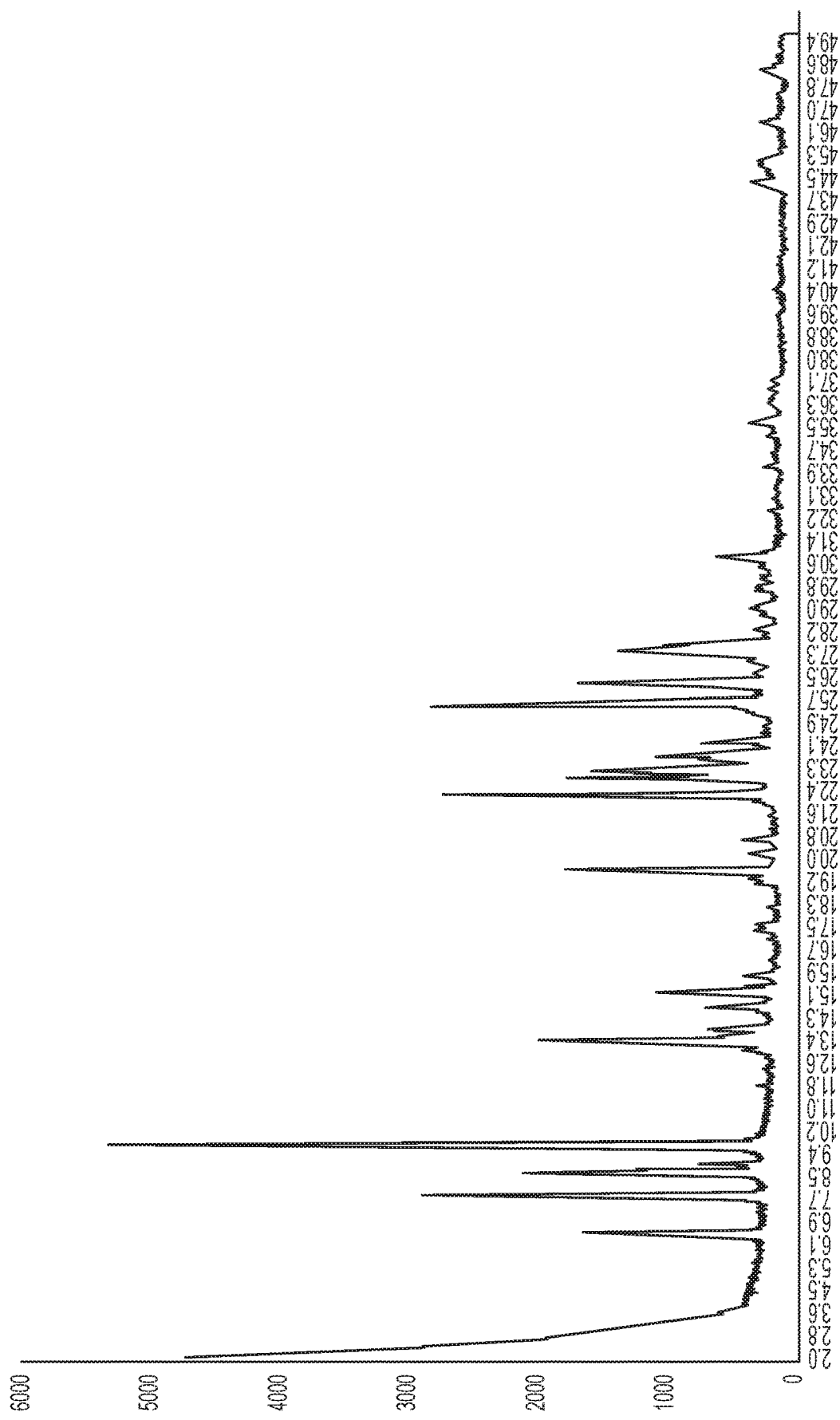
FIG. 8 is an XRD graph of a zeolite composite catalyst which was produced through the physical mixture of commercial samples of mordenite and ZSM-5 in their ammonia form.

The XRD pattern for Comparative Example 6 (Catalyst F) is provided in FIG. 8.

Comparative Example 7: Only Mordenite Treated with 0.4 N NaOH Solution Followed by Still Crystallization in the Presence of CTAB and Physically Mixed with Untreated Commercial ZSM-5

Mordenite (Si/Al molar ratio=30), HSZ-660HOA, was disintegrated using 0.40M NaOH solution by gradual heating (without stirring) at 100° C. for 24 hours (h). The heating was carried out in the presence of CTAB (4.45 wt. %). The mixture was cooled down and then the pH was adjusted to 9.0 through the addition of dilute sulfuric acid (2N). The mixture was then stirred for 24 hours (h) and then aged at 100° C. for 24 h to form a solid zeolite composite of mordenite and ZSM-5 respectively. The solid zeolite composite was filtered, washed thoroughly using distilled water, dried at 80° C. overnight, then calcined at 550° C. for 6 h to remove the surfactant (CTAB). The solid composite material (mordenite) thus obtained was ion-exchanged three times with 0.05 M NH4NO3 solution at 80° C. for 5 h. The resulting zeolite meso-structured mordenite was physically mixed in a 3:1 weight ratio with untreated ZSM-5 in its ammoniated form and made into extrudates by mixing 67 wt. % solid zeolite composite (mordenite+ZSM-5 at 3:1 weight ratio) and 33 wt. % alumina binder (Cataloid AP-3). Then, the mordenite+ZSM-5 at a 3:1 weight ratio was loaded with 4 wt. % of molybdenum in the form of ammonium molybdate tetrahydrate through wet impregnation. Then, the impregnated solid zeolite was calcined at 450° C. for 5 h. The resulting zeolite mordenite/ZSM-5 composite is designated as Comparative Example 7 (Catalyst G). Table 8 includes selected properties of Comparative Example 7 (Catalyst G).

TABLE 8

Comparative Example 7 (Catalyst G) Data

| Catalyst | BET Surface Area ($m^2/g$) | Micropore Surface Area ($m^2/g$) | External Surface Area ($m^2/g$) | Total Pore Volume ($cm^3/g$) | Micropore Volume ($cm^3/g$) | Mesopore Volume ($cm^3/g$) |
|---|---|---|---|---|---|---|
| Comparative Example 7 (Catalyst G) | 488 | 354 | 135 | 0.4023 | 0.171 | 0.2313 |

Figure 9:
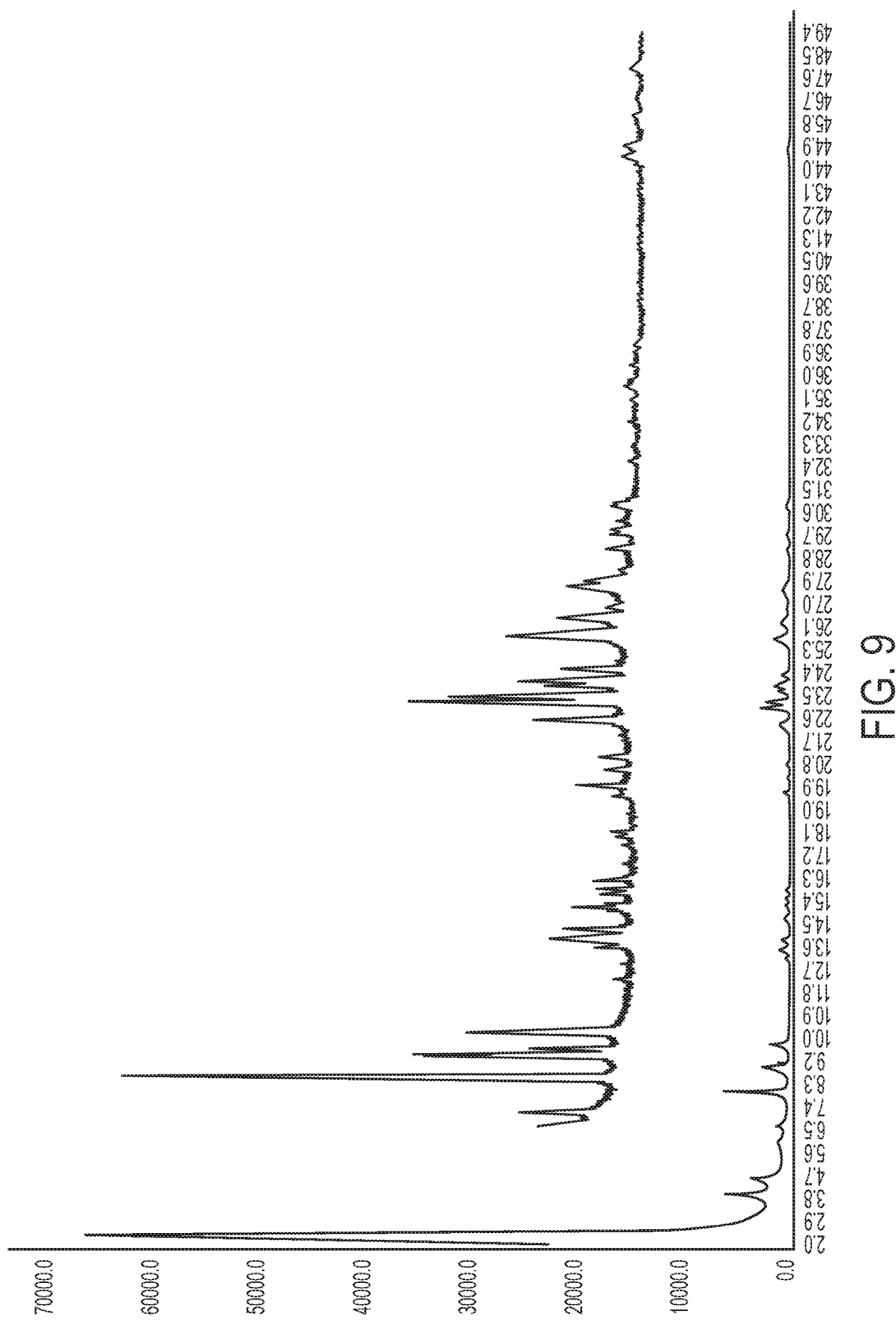
FIG. 9 is an XRD graph of a zeolite composite catalyst having an ordered hexagonal mesophase and a disordered hexagonal mesophase, which was produced through the dissolution of mordenite using 0.4M NaOH solution in the presence of still CTAB and then physically mixed with untreated commercial ZSM-5 in its ammonia form.

The dissolution of mordentite using 0.40M NaOH solution and still crystallization in the presence of CTAB leads to meso-structure formation with ordered and disordered mesophase as shown in the XRD pattern in FIG. 9. FIG. 9 provides the XRD pattern for the treated mordenite physically mixed with untreated commercial ZSM-5 in ammonia form.

Comparative Example 8: Only ZSM-5 Treated with 0.4 N NaOH Solution Followed by Still Crystallization in the Presence of CTAB and Physically Mixed with Untreated Commercial Mordenite ZSM-5 (Si/Al molar ratio=40), HSZ-840NHA, was disintegrated using 0.40M NaOH solution by gradual heating (without stirring) at 100° C. for 24 hours (h). The heating was carried out in the presence of CTAB (4.45 wt. %). The mixture was cooled down and then the pH was adjusted to 9.0 through the addition of dilute sulfuric acid (2N). The mixture was then stirred for 24 hours (h) and then aged at 100° C. for 24 h to form a solid zeolite composite of mordenite and ZSM-5 respectively. The solid zeolite composite was filtered, washed thoroughly using distilled water, dried at 80° C. overnight, then calcined at 550° C. for 6 h to remove the surfactant (CTAB). The solid composite material (ZSM-5) thus obtained was ion-exchanged three times with 0.05 M NH4NO3 solution at 80° C. for 5 h. The resulting zeolite meso-structured ZSM-5 was physically mixed in a 1:3 weight ratio with untreated mordenite in its ammoniated form and made into extrudates by mixing 67 wt. % solid zeolite composite (mordenite+ZSM-5 at 3:1 weight ratio) and 33 wt. % alumina binder (Cataloid AP-3). Then the mordenite+ZSM-5 at a 3:1 weight ratio were loaded with 4 wt. % of molybdenum in the form of ammonium molybdate tetrahydrate through wet impregnation. Then, the impregnated solid zeolite was calcined at 450° C. for 5 h. The resulting zeolite mordenite/ZSM-5 composite is designated as Comparative Example 8 (Catalyst H). Table 9 includes selected properties of Comparative Example 8 (Catalyst H).

TABLE 9

Comparative Example 8 (Catalyst H) Data

| Catalyst | BET Surface Area (m²/g) | Micropore Surface Area (m²/g) | External Surface Area (m²/g) | Total Pore Volume (cm³/g) | Micropore Volume (cm³/g) | Mesopore Volume (cm³/g) |
|---|---|---|---|---|---|---|
| Comparative Example 8 (Catalyst H) | 468 | 213 | 255 | 0.5512 | 0.098 | 0.4532 |

Figure 10:
FIG. 10 is an XRD graph of a zeolite composite catalyst having an ordered hexagonal mesophase and a disordered hexagonal mesophase, which was produced through the dissolution of ZSM-5 using 0.4M NaOH solution in the presence of still CTAB and then physically mixed with untreated commercial mordenite in its ammonia form.

The dissolution of ZSM-5 using 0.40M NaOH solution and still crystallization in the presence of CTAB leads to meso-structure formation with ordered and disordered mesophase as shown in the XRD pattern in FIG. 10. FIG. 10 provides the XRD pattern for the treated mordenite physically mixed with untreated commercial mordenite in ammonia form.

TABLE 10

Heavy reformate composition

| Major Hydrocarbons | Amount (wt. %) |
|---|---|
| p-Xylene | 0.22 |
| m-Xylene | 0.52 |
| o-Xylene | 4.17 |
| n-Propylbenzene | 2.54 |
| p + m Methylethylbenzene | 16.50 |
| 1,3,5 Trimethylbenzene | 12.00 |
| o-MethylEthylbenzene | 4.62 |
| 1,2,4, Trimethylbenzene | 37.70 |
| 1,2,3 Trimethylbenzene | 6.85 |
| Total C8 Components | 4.91 |
| Total C9 Components | 80.21 |
| Total C10 Components | 8.15 |
| Total C11 Components | 6.11 |

Activity studies for Catalysts A, B, C, D, E, F, G, H represented in Table 1 were performed on a bench top reactor using industrial reformate feedstock (formulation provided infra in Table 10). The procedure used for determination of catalytic activity for each catalyst of Table 1 individually consisted of loading a vertical reactor with 1.0 gram of the catalyst in the isothermal zone of the reactor together with an inert silicon carbide in the lower and upper parts of the reactor. The total volume of the reactor was 20 ml. The catalyst was activated and reduced under 50 ml/min flow of pure hydrogen gas at 450° C. and was kept at this temperature for 2 hours. Then, the pressure of the reactor was increased to 20 bar and the flow of the industrial reformate feedstock was started at 4.2 grams/h. The reaction was allowed to run at least one hour at 400° C. before collecting the product sample. The reactor was allowed to further run for 48 hours without exhibiting loss of activity before termination. The liquid product obtained from the reactor was analyzed using a gas chromatograph. The reaction product was directly injected into an on-line gas chromatograph equipped with one thermal conductivity detector (TCD) and two flame ionization detector. The gas chromatography uses a plurality of columns to conduct the analysis of the liquid product obtained from the reactor. A Hayesep N pre-column with a 0.5 meter (m) length, a Hayesep Q column with a 1.5 m length, a CP-Wax capillary column with a 5.0 m length and 0.32 mm inner diameter, and a 13C molecular sieve with a 1.2 m length were utilized. Each column was manufactured by Agilent Technologies (Santa Clara, Calif.). Table 11 The experimental results provided in Table 11 shows the comparison of the gas chromatograph liquid product analysis of Catalysts A, B, C, D, E, F, G, H.

TABLE 11

Catalyst Experimental results

| Catalyst | Average MEB Conversion (wt. %) | Average TMB Conversion (wt. %) | Average total xylenes yield (wt. %) | Average total toluene yield (wt. %) | Average benzene yield (wt. %) |
|---|---|---|---|---|---|
| Catalyst A (Example 1) | 96.8 | 39.7 | 37.7 | 15.2 | 1.8 |
| Catalyst B (Example 2) | 96.9 | 40.8 | 38.1 | 15.5 | 1.8 |
| Catalyst C (Example 3) | 97.41 | 44 | 39 | 17.03 | 2.15 |
| Catalyst D (Comparative Example 4) | 93.3 | 41.2 | 36.9 | 14.5 | 1.7 |
| Catalyst E (Comparative Example 5) | 98.62 | 4.55 | 17.94 | 17.44 | 2.66 |
| Catalyst F (Comparative Example 6) | 97.7 | 36.7 | 36.2 | 14.1 | 1.7 |
| Catalyst G (Comparative Example 7) | 96 | 37 | 37 | 14 | 2 |
| Catalyst H (Comparative Example 8) | 98.3 | 35.2 | 37.3 | 14.2 | 1.6 |

Table 11 allow for the determination of effect of the meso-structured Mordenite and ZSM-5. Catalyst F (Comparative Example 6) represents a mix of untreated commercial samples of Mordenite and ZSM-5. Comparison of Catalyst F (Comparative Example 6) with Catalysts A, B, and C (Examples 1, 2, and 3 respectively) provides indication of the improved yields provided by the treated Mordenite and ZSM-5. Catalyst F (Comparative Example 6) resulted in a yield of 36.2 wt. % of xylenes and Catalyst A (Example 1), which is a hierarchical composite of Mordenite and ZSM-5 in 3:1 ratio as described supra, resulted in a yield of 37.7 wt. % of xylenes. This represents a 1.5 wt. % increase. This increase can be explained due to the structure of Mordenite and ZSM-5 in Catalyst A (Example 1) which improved the transport properties which in turn boosted the conversion of trimethylbenzenes from 36.7 wt. % with Catalyst F (Comparative Example 6) to 39.7 wt. % with Catalyst A (Example 1). When an agitated recrystallization procedure was used with Catalyst B (Example B), an even better result was achieved. Specifically, Catalyst B (Example B) exhibited a 38.1 wt. % xylenes yield representing a 1.9% increase over Catalyst F (Comparative Example 6). Yet an even better result was achieved when Mordenite and ZSM-5 were separately treated and physically mixed in a 3:1 ratio after recrystallization as in Catalyst C (Example 3). Specifically, Catalyst C (Example 3) exhibited a 39 wt. % xylenes yield representing a 2.8 wt. % increase over Catalyst F (Comparative Example 6).

The catalysts G (Comparative Example 7) and H (Comparative Example 8) were synthesized with one treated component (either Mordenite or ZSM-5) and one other untreated component (the other of Mordenite or ZSM-5) to understand the effect of treatment on both the components and overall catalyst formulation. Catalyst G (Comparative Example 7) represented a physically mixture of 3 parts of treated Mordenite and one part of commercial untreated ZSM-5 while Catalyst H (Comparative Example 8) represented a physically mixture of 3 parts of commercial untreated Mordenite and one part of treated ZSM-5. Both Catalyst G (Comparative Example 7) and Catalyst H (Comparative Example 8) resulted in similar xylenes yields of 37 and 37.3, respectively. These xylene yields represent an increase of 0.8 and 1.1 wt. % respectively over Catalyst F (Comparative Example 6). However, the xylene yield of Catalyst G (Comparative Example 7) and Catalyst H (Comparative Example 8) is notably less than the xylene yield of Catalysts A, B, and C (Examples 1, 2, and 3 respecitvly), which comprise treated Mordenite and treated ZSM-5. These results illustrated the desirability of both components (mordenite and ZSM-5) to be treated for obtaining higher xylene yields.

It is noted that Catalyst G (Comparative Example 7) which has the treated Mordenite component demonstrated higher Trimethylbenzenes conversion compare to Catalyst H which is comprised of untreated Mordenite, indicating the treated mordentite has higher capabilities of trimethylbenzene conversion or transalkylation with toluene. Similarly, Catalyst H (Comparative Example 8) was made with treated ZSM-5 and Catalyst G (Comparative Example 7) with untreated ZSM-5, and Catalyst H (Comparative Example 8) demonstrated higher methylethylbenzenes conversion of 98.3 wt. % compared to Catalyst G (Comparative Example 7) of 96 wt. %. Based on these observations we can infer that the treated Mordenite contributes to higher trimethylbenzenes conversion or trans alkylations and treated ZSM-5 leads to higher methylethylbenzenes conversions, both transformations together have prime contributions towards formation of xylenes.

A treated Mordenite alone, Catalyst D (Comparative Example 4), resulted in a yield of 36.9 wt. % xylenes which is 0.7% more than Catalyst F. However, Catalyst D (Comparative Example 4) has a 41.2 wt. % conversion of trimethylbenzenes and only a 93.3 wt. % ethylmethylbenzenes conversion, which again indicates that treated Mordenite is a more efficient transalkylating agent than de-alkylating agent.

A treated ZSM-5 alone, Catalyst E (Comparative Example 5), resulted in a yield of only 17.94 wt. % of xylenes with only 4.55 wt. % of trimethylbenzenes conversion. This conversion of trimethylbenzenes and xylene yield is far less than any of the other catalyst formulations. However, the efficiency of Catalyst E (Comparative Example 5) in methylethylbenzenes conversion is the highest among all the catalyst formulations at 98.62 wt. % which is directly translated to the highest toluene yield of 17.44 wt. %.

It should now be understood the various aspects of the hierarchical composite zeolite catalysts, the methods of producing a hierarchical zeolite composite, and the methods of converting $C_{9+}$ alkyl aromatic hydrocarbons to a product stream comprising benzene, toluene, and xylene using the same are described and such aspects may be utilized in conjunction with various other aspects.

In a first aspect, the disclosure provides a method of producing a hierarchical zeolite composite catalyst. The method comprises dissolving, in an alkaline solution and in the presence of a surfactant, a catalyst precursor comprising mesoporous zeolite while heating, stirring, or both to yield a dissolved zeolite solution, where the mesoporous zeolite comprises large pore mordenite, medium pore ZSM-5, or large pore mordenite and medium pore ZSM-5. The method further comprises condensing the dissolved zeolite solution to yield a solid zeolite composite from the dissolved zeolite solution, where condensing the dissolved zeolite solution comprises adjusting a pH of the dissolved zeolite solution and aging the pH adjusted dissolved zeolite solution. The method yet further comprises heating the solid zeolite composite to remove the surfactant; impregnating the solid zeolite composite with one or more active metals selected from the group consisting of molybdenum, platinum, rhenium, nickel, and combinations thereof to yield impregnated solid zeolite composite; and calcining the impregnated solid zeolite composite to produce the hierarchical zeolite composite catalyst. The produced hierarchical zeolite composite catalyst has a mesostructure comprising at least one disordered mesophase and at least one ordered mesophase.

In a second aspect, the disclosure provides the method of the first aspect, in which the method further comprises extruding the solid zeolite composite with binder.

In a third aspect, the disclosure provides the method of the second aspect, in which the binder is an alumina based binder.

In a fourth aspect, the disclosure provides the method of the second aspect, in which a ratio by weight of the solid zeolite composite to binder is 2 to 1.

In a fifth aspect, the disclosure provides the method of any of the first through fourth aspects, in which the mordenite comprises pores formed from 12 membered rings forming a framework of the zeolite and the ZSM-5 comprises pores formed from 10 membered rings forming the framework of the zeolite.

In a sixth aspect, the disclosure provides the method of any of the first through fifth aspects, in which the ordered mesophase is a hexagonal mesophase.

In a seventh aspect, the disclosure provides the method of any of the first through sixth aspects, in which the condensing is performed under still conditions.

In an eighth aspect, the disclosure provides the method of any of the first through sixth aspects, in which the condensing is performed under agitated conditions.

In a ninth aspect, the disclosure provides the method of any of the first through eighth aspects, in which the heating is hydrothermal heating.

In a tenth aspect, the disclosure provides the method of any of the first through ninth aspects, in which the aging involves maintaining the pH adjusted dissolved zeolite solution at a temperature of 75 to 125° C. for a duration of 12 to 48 hours.

In an eleventh aspect, the disclosure provides the method of any of the first through tenth aspects, in which the mordenite has a Si/Al ratio of 20 to 300 and the ZSM-5 has a Si/Al ratio of 5 to 500.

In a twelfth aspect, the disclosure provides the method of any of the first through eleventh aspects, in which a ratio of mordenite to ZSM-5 is 1:1 to 5:1 by weight.

In a thirteenth aspect, the disclosure provides the method of any of the first through twelfth aspects, in which a ratio of mordenite to ZSM-5 is 3:1 by weight.

In a fourteenth aspect, the disclosure provides the method of any of the first through thirteenth aspects, in which the method further comprises ion exchanging the solid zeolite composite.

In a fifteenth aspect, the disclosure provides the method of any of the first through fourteenth aspects, in which the surfactant is cetyltrimethyl ammonium bromide.

In a sixteenth aspect, the disclosure provides the method of the fifteenth aspect, in which the cetyltrimethyl ammonium bromide comprises 1 to 8 wt. % of the dissolved zeolite solution.

In a seventeenth aspect, the disclosure provides the method of any of the first through sixteenth aspects, in which the catalyst precursor further comprises at least one additional mesoporous zeolite selected from the group consisting of ZSM-22, ZSM-12, and combinations thereof.

In an eighteenth aspect, the disclosure provides the method of any of the first through seventeenth aspects, in which the adjusting of the pH is performed by an acidic solution to adjust the pH to less than 9.

In a nineteenth aspect, the disclosure provides the method of any of the first through eighteenth aspects, in which the zeolite composite catalyst has a pore volume ranging from 0.2 to 3.0 cm$^3$/g.

In a twentieth aspect, the disclosure provides the method of any of the first through nineteenth aspects, in which a molar ratio of silica to aluminum in the zeolite composite catalyst is from 18 to 500.

In a twenty-first aspect, the disclosure provides the method of any of the first through twentieth aspects, in which the active metals comprise molybdenum.

In a twenty-second aspect, the disclosure provides the method of any of the first through twenty-first aspects, in which the active metals comprises 0.01 to 6.0 wt. % of the impregnated solid zeolite composite.

In a twenty-third aspect, the disclosure provides the method of any of the first through twenty-second aspects, in which the alkaline solution is a 0.1 to 0.6 M NaOH solution.

In a twenty-fourth aspect, the disclosure provides a method of converting $C_{9+}$ alkyl aromatic hydrocarbons to a product stream comprising benzene, toluene, and xylene. The method comprises reducing a hierarchical zeolite composite catalyst comprising a mesostructure comprising at least one disordered mesophase and at least one ordered mesophase with hydrogen gas at 400 to 500° C. The hierarchical zeolite composite catalyst comprises large pore mordenite, medium pore ZSM-5, and one or more impregnated active metals. The method further comprises contacting a feed comprising $C_{9+}$ alkylaromatic hydrocarbons with the reduced composite zeolite catalyst and hydrogen in a transalkylation zone of a reactor to produce a transalkylation product, stripping $C_1$-$C_5$ and unreacted feed from the transalkylation product, and collecting at least the xylenes product from the transalkylation product.

In a twenty-fifth aspect, the disclosure provides the method of the twenty-fourth aspect, in which the transalkylation zone is at a pressure between 1.0 to 3.0 MPa, a temperature of 200° C. to 500° C., a space velocity of 1.0 to 5.0 h$^{-1}$, and a hydrogen to hydrocarbon ratio of 1 to 4.

In a twenty-sixth aspect aspect, the disclosure provides the method of the twenty-fourth or twenty-fifth aspects, in which the one or more active metals are selected from the group consisting of molybdenum, platinum, rhenium, nickel, and combinations thereof.

In a twenty-seventh aspect, the disclosure provides a hierarchical zeolite composite catalyst. The hierarchical zeolite composite catalyst comprises a solid zeolite composite mixed with an alumina binder. The solid zeolite composite comprises a large pore mordenite and a medium pore ZSM-5 in a 1:1 to 5:1 weight ratio. Further, the hierarchical zeolite composite catalyst has a mesostructure comprising at least one disordered mesophase and at least one ordered mesophase.

In a twenty-eighth aspect, the disclosure provides a method of any of the first through twenty-third aspects in which the mesoporous zeolite comprises large pore mordenite.

In a twenty-ninth aspect, the disclosure provides a method of any of the first through twenty-third aspects in which the mesoporous zeolite comprises medium pore ZSM-5.

In a thirtieth aspect, the disclosure provides a method of any of the first through twenty-third aspects in which the mesoporous zeolite comprises large pore mordenite and medium pore ZSM-5.

It should be apparent to those skilled in the art that various modifications and variations can be made to the described embodiments without departing from the spirit and scope of the claimed subject matter. Thus, it is intended that the specification cover the modifications and variations of the various described embodiments provided such modification and variations come within the scope of the appended claims and their equivalents.

Throughout this disclosure ranges are provided. It is envisioned that each discrete value encompassed by the ranges are also included. Additionally, the ranges which may be formed by each discrete value encompassed by the explicitly disclosed ranges are equally envisioned.

What is claimed is:

1. A method of producing a hierarchical zeolite composite catalyst comprising:
    dissolving, in an alkaline solution and in the presence of a surfactant, a catalyst precursor comprising zeolite while heating, stirring, or both to yield a dissolved zeolite solution, where the zeolite comprises both mordenite and ZSM-5 at a ratio of mordenite to ZSM-5 of 1:1 to 5:1 by weight and where the alkaline solution is a 0.1 to 0.6 M NaOH solution;
    condensing the dissolved zeolite solution to yield a solid zeolite composite from the dissolved zeolite solution, where condensing the dissolved zeolite solution comprises:
        adjusting a pH of the dissolved zeolite solution; and
        aging the pH adjusted dissolved zeolite solution;
    heating the solid zeolite composite to remove the surfactant;
    impregnating the solid zeolite composite with one or more active metals selected from the group consisting of molybdenum, platinum, rhenium, nickel, and combinations thereof to yield impregnated solid zeolite composite; and
    calcining the impregnated solid zeolite composite to produce the hierarchical zeolite composite catalyst, where the hierarchical zeolite composite catalyst has a mesostructure comprising at least one disordered mesophase and at least one ordered mesophase and where the hierarchical zeolite composite catalyst comprises an average pore diameter of 3 nm to 3.5 nm.

2. The method of claim 1 further comprising extruding the solid zeolite composite with binder.

3. The method of claim 2 where the binder is an alumina based binder.

4. The method of claim 1 where the ordered mesophase is a hexagonal mesophase.

5. The method of claim 1 where the aging involves maintaining the pH adjusted dissolved zeolite solution at a temperature of 75 to 125° C. for a duration of 12 to 48 hours.

6. The method of claim 1 where the mordenite has a Si/Al molar ratio of 20 to 300 and the ZSM-5 has a Si/Al molar ratio of 5 to 500.

7. The method of claim 1 further comprising ion exchanging the solid zeolite composite.

8. The method of claim 1 where the surfactant is cetyltrimethyl ammonium bromide and the dissolved zeolite solution comprises 1 to 8 wt. % of the cetyltrimethyl ammonium bromide.

9. The method of claim 1 where the adjusting of the pH is performed by an acidic solution to adjust the pH to less than 9.

10. The method of claim 1 where the zeolite composite catalyst has a pore volume ranging from 0.2 to 3.0 cm$^3$/g.

11. The method of claim 1 where a molar ratio of silica to aluminum in the zeolite composite catalyst is from 18 to 500.

12. The method of claim 1 where the active metals comprises 0.01 to 6.0 wt. % of the impregnated solid zeolite composite.

13. The method of claim 1 where the alkaline solution is a 0.35 to 0.45 M NaOH solution.

\* \* \* \* \*